United States Patent [19]
Kopchick et al.

[11] Patent Number: 6,080,911
[45] Date of Patent: Jun. 27, 2000

[54] MICE MODELS OF GROWTH HORMONE INSENSITIVITY

[75] Inventors: John J. Kopchick, Athens, Ohio; Yihua Zhou, St. Louis, Miss.

[73] Assignee: Ohio University, Athens, Ohio

[21] Appl. No.: 08/834,314

[22] Filed: Apr. 15, 1997

[51] Int. Cl.$^7$ ............................ C12N 15/09; C12N 15/63; C12N 15/00; C12N 5/00

[52] U.S. Cl. ............................ 800/18; 800/3; 800/9; 800/21; 800/22; 800/25; 435/455; 435/463; 435/320.1; 435/325

[58] Field of Search .............................. 800/2, 18, 3, 9, 800/21, 22, 25; 435/455, 463, 320.1, 325

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,873,191 | 10/1989 | Wagner et al. | 435/172.3 |
| 4,965,188 | 10/1990 | Mullis et al. | 435/6 |
| 5,689,050 | 11/1997 | Thomas et al. | 800/205 |

FOREIGN PATENT DOCUMENTS

WO 90/08832 of 1990 WIPO.

OTHER PUBLICATIONS

Rechler et al. (1987) N. Engl. J. Med. 316:941.
Hughes and Friesen (1985) Ann. Rev. Physiol. 47:469.
Isaksson et al. (1985) Ann. Rev. Physiol. 47:483.
Xu et al. (1996) "Growth Hormone Promotes the Association of Transcription Factor STAT5 with the Growth Hormone Receptor," J. Biol. Chem. 271:19768–19770.
Wang et al. (1996) "Identification of Growth Hormone Receptor (GHR) Tyrosine Residues Required for GHR Phosphorylation and JAK2 and STAT5 Activation," Mol. Endocrinol. 10:1249–1260.
Baumann and Shaw (1990) J. Clin. Endocrinol. Metab. 70:680.
Peeters and Friesen (1977) Endocrinol. 101:1164.
Baumann et al. (1986) J. Clin. Endocrinol. Metab. 62:134.
Herington et al. (1986) J. Clin. Invest. 7:1817.
Leung et al. (1987) Nature 330:537.
Herington et al. (1986) Biochem. Biophys. Res. Commun. 139:150.
Hocquette et al. (1990) Endocrinol. 127:1665.
Smith and Talamantes (1988) Endocrinol. 123:1489.
Trivedi et al. (1988) Endocrinol. 123:2201.
Sotiropoulos et al. (1993) Endocrinol. 132:1863.
Baumbach et al. (1989) Genes Devel. 3:1199.
Baumann (1993) Proc. Soc. Exp. Biol. Med. 202:392.
Baumann (1994) J. Endocrinol. 141:1.
Maheshwari et al. (1996) J. Clin. Endocrinol. Metab. 81:995.
Baumann et al. (1987) J. Clin. Endocrinol. Metab. 65:814.
Daughaday and Trivedi (1987) Proc. Natl. Acad. Sci. USA 84:4636.
Rieu et al. (1993) J. Clin. Endocrinol. Metab. 76:857.

Godowski et al. (1989) "Characterization of the human growth hormone receptor gene and demonstration of a partial gene deletion in two patients with Laron–type dwarfism," Proc. Natl. Acad. Sci. USA 86:8083–8087.
Berg et al. (1993) "Diverse Growth Hormone Receptor Gene Mutations in Laron Cyndrome," Am. J. Hum. Genetics 52:998–1005.
Amelselem et al. (1993) "Spectrum of growth hormone receptor mutations and associated haplotypes in Laron syndrome," Human Mol. Genetics 2:355–359.
Rosenbloom et al. (1990) N. Engl. J. Med. 323:1367.
Savage et al. (1993) "Clinical Features and Endocrine Status in Patients with Growth Hormone Insensitivity (Laron Syndrome)," J. Clin. Endocrinol. Metab. 77:1465–1471.
Woods et al. (1996) J. Clin. Endocrinol. Metab. 81:1686.
Duquesnoy et al. (1994) EMBO J. 13:1386.
Kou et al. (1993) J. Clin. Endocrinol. Metab. 76:54.
Goddard et al. (1995) "Mutations of the Growth Hormone Receptor in Children with Idiopathic Short Stature," N. Engl. J. Med. 333:1093–1098.
Rosenfeld et al. (1994) Endo Rev. 15:369.
Walker et al. (1991) "Effects of the Infusion of Insulin–Like Growth Factor I in a Child with Growth Hormone Insensitivity Syndrome (Laron Dwarfism)," N. Engl. J. Med. 324:1483–1488.
Brinster et al. (1985) "Factors affecting the efficiency of introducing foreign DNA into mice by microinjecting eggs," Proc. Natl. Acad. Sci. USA 82:4438–4442.
Jaenisch (1976) "Germ line integration and Mendelian transmission of the exogenous Moloney leukemia virus," Proc. Natl. Acad. Sci USA 73:1260–1264.
Jahner et al. (1985) "Insertion of the bacterial gpt gene into the germ line of mice by retroviral infection," Proc. Natl. Acad. Sci. USA 82:6927–6931.
Van der Putten et al. (1985) "Efficient insertion of genes into the mouse germ line via retroviral vectors," Proc. Natl. Acad Sci USA 82:6148–6152.
Stewart et al. (1987) "Expression of retroviral vectors in transgenic mice obtained by embryo infection," EMBO 6:383–388.
Jahner et al. (1982) "De novo methylation and expression of retroviral genomes during mouse embryogenesis," Nature 298:623–628.
Zhou et al. (1994) "An Exon Encoding the Mouse Growth Hormone Binding Protein (mGHBP) Carboxy Terminus is Located Between Exon 7 and 8 of the Mouse Growth Hormone Receptor Gene," Receptor 4:223–227.

(List continued on next page.)

*Primary Examiner*—Bruce R. Campell
*Assistant Examiner*—Jill D. Martin
*Attorney, Agent, or Firm*—Medlen & Carroll, LLP

[57] ABSTRACT

The present invention provides mouse models of growth hormone insensitivity including Laron syndrome. In particular, the present invention provides transgenic mice incapable of expressing functional growth hormone receptor including mice which further cannot express functional growth hormone binding protein. The invention further provides methods for testing the usefulness of chemical compounds in the treatment of growth hormone insensitivity and diabetic end-organ disease.

14 Claims, 12 Drawing Sheets

OTHER PUBLICATIONS

Zhou et al.(1996) Gene 177:257.
Herington et al. (1991) Acta Endocrinol. 124:14.
Walker et al. (1992) Pediatric Res. 31:335.
Garcia–Aragon et al. (1992) Development 114:869.
Laron et al. (1988) "Effect of Acute Administration of Insulin–Like Growth Factor I in Patients with Laron–Type Dwarfism," Lancet 2:1170–1172.
Guler et al. (1989) Proc. Natl. Acad. Sci. USA 86:2868.
Guler et al. (1987) N. Engl. J. Med. 317:137.
Burnside et al. (1992) "Abnormal Growth Hormone Receptor Gene Expression in the Sex–Linked Dwarf Chicken," Gen. Com. Endocrinol. 88:20–28.
Burnside (1991) "Molecular Cloning of the Chicken Growth Hormone Receptor Complementary Deoxyribonucleic Acid: Mutation of the Gene in Sex–Linked Dwarf Chickens," Endocrinol. 128:3183–3192.
Huang (1993) Lab. Animal Sci. 43:156.
Strauss et al. (1996) Science 273:1386.
Salem and Wohff (1989) Proc. Soc. Exp. Biol. Med. 191:113.
Chipkin et al. (1989) Endocrinol. 125:450.
Davidson (1987) Endocr. Rev. 8:115.
Gerich (1986) Scand J. Gastroenterol. 21 (Suppl. 119):154.
Holly et al. (1988) J. Endocrinol. 118:353.
Yang et al. (1993) Lab. Invest. 68:62.
Chen et al. (1995) "Effects of Streptozotocin Treatment in Growth Hormone (GH) and GH Antagonist Transgenic Mice," Endocrinol. 136:660–667.
Chen et al. (1996) "A Growth Hormone Antagonist Protects Mice Against Streptozotocin Induced Glomerulosclerosis Even in the Presence of Elevated Levels of Glucose and Glycated Hemoglobin," Endocrinol. 137:5163–5165.
Alzaid et al. (1994) Diabetes Care 17:531.
Brown–Borg et al. (1996) Nature 384:33.
Steger et al. (1993) J. Reprod. Fertil. Suppl. 46:61.
Pendergrass et al. (1993) J. Cell. Physiol. 156:96.
Chauhan et al. (1992) Gene 120:281.
Bass et al. (1991) Proc. Natl. Acad. Sci. USA 88:4498.
Amselem et al. (1991) J. Clin. Invest. 87:1098.
De Vos et al. (1992) Science 255:306.
Robberson et al. (1990) Mol. Cell. Biol. 10:84.
Hooper et al. (1987) Nature 326:292.
Williams et al. (1988) Nature 336:684.
Hogan et al. (1994) *Manipulating the Mouse Embryo: A Laboratory Manual,* 2nd Ed., Cold Spring Harbor Laboratory Press, NY.
Ramirez–Solis et al. (1992) Analytical Biochem. 201:331.
Kuehn et al. (1987) Nature 326:295.
Rosenbloom et al. (1992) Acta Pediatr. (Suppl.) 383:121.
Daughaday et al. (1980) J. Clin. Endocrinol. Metab. 51:781.
Chen et al. (1991) Endocrinol. 128:1402.
Sinha et al. (1972) Endocrinol. 91:784.
He et al., abstract P3–213, "A GT Repeating Sequence in the Mouse Growth Hormone Receptor (mGHR)/Binding Protein (mGHBP) Gene is Essential for Generating mGHR and mGHBP mRNAs.
Saito et al. (1992) "Bovine embryonic stem cell–like cell lines cultured over several passages," Roux's Arch. Dev. Biol. 201:134–141.
Stice et al. (1996) "Pluripotent Bovine Embryonic Cell Lines Direct Embryonic Development Following Nuclear Transfer," Biol. of Reprod. 54:100–110.
Zhou et al., abstract P3–212, "Deletion of the Mouse Growth Hormone Binding Protein (mGHBP) Poly–Adenylation Signal(s) Does Not Inhibit mGHBP Production.
Moreadith et al., J. Mol. Med., vol. 75, pp. 208–216, 1997.
Capecchi, Scientific American, vol. 270, No. 3, pp. 34–41, Mar. 1994.
Zhou et al., Receptor, vol. 4, No. 4, pp. 223–227 (Abstract only), 1994.
Westphal, FASEB J., vol. 3, pp. 117–120, 1989.
Fouchereau–Peron et al. (Biochimica et Biophysica Acta, (Sep. 1, 1980) 631 (3) 451–62).
Agarwal et al. Journal of Endocrinology 142 (3) 1994. 427–434.
Barnard et al. (Growth Regulation, (Dec. 1994) 4 (4) 147–54).
Sandstedt et al. (Acta Paediatrica Supplement O (417). Apr. 1996. 139 ).
Vasilatos–Younken et al. (General and Comparative Endocrinology 105 (1). 1997. 31–39).
Duriez et al. (Mol Endocrinol 7 (6). 1993, 806–814).
Edens et al. (Endocrinology 135 (6). 1994 1994, 2802–2805).
Charreau et al. (Transgenic Research, (Jul. 1996) 5 (4) 223–34).
Fleay in 1944 (Augee, 1992).

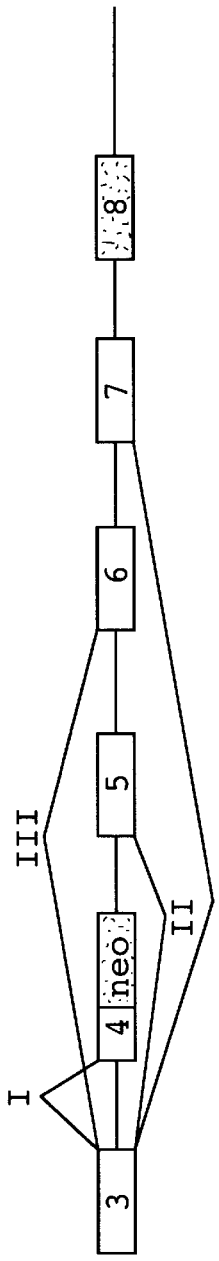

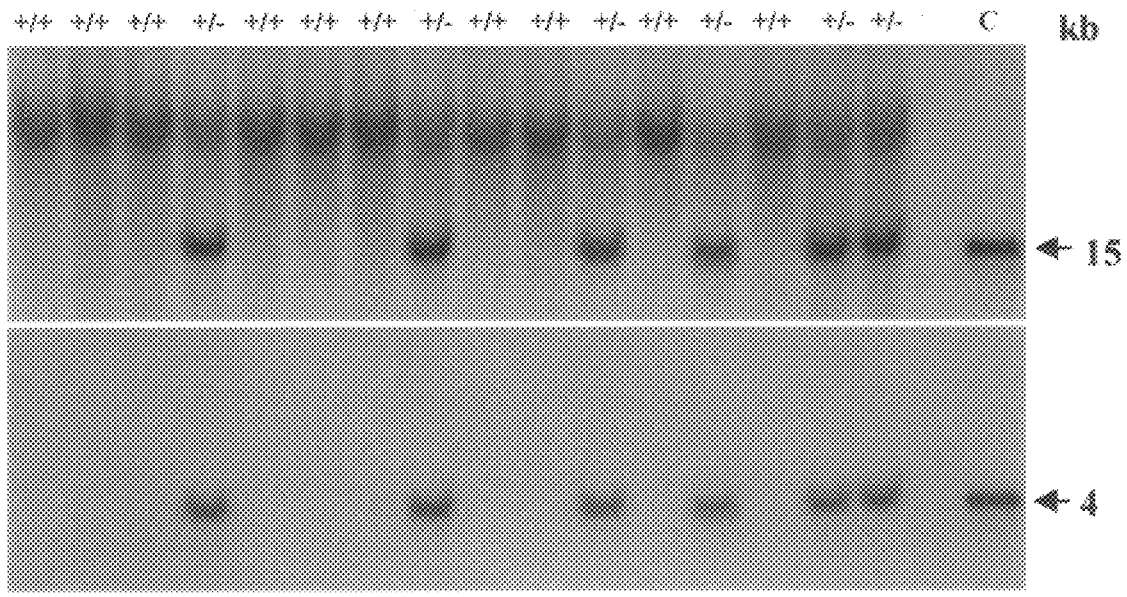
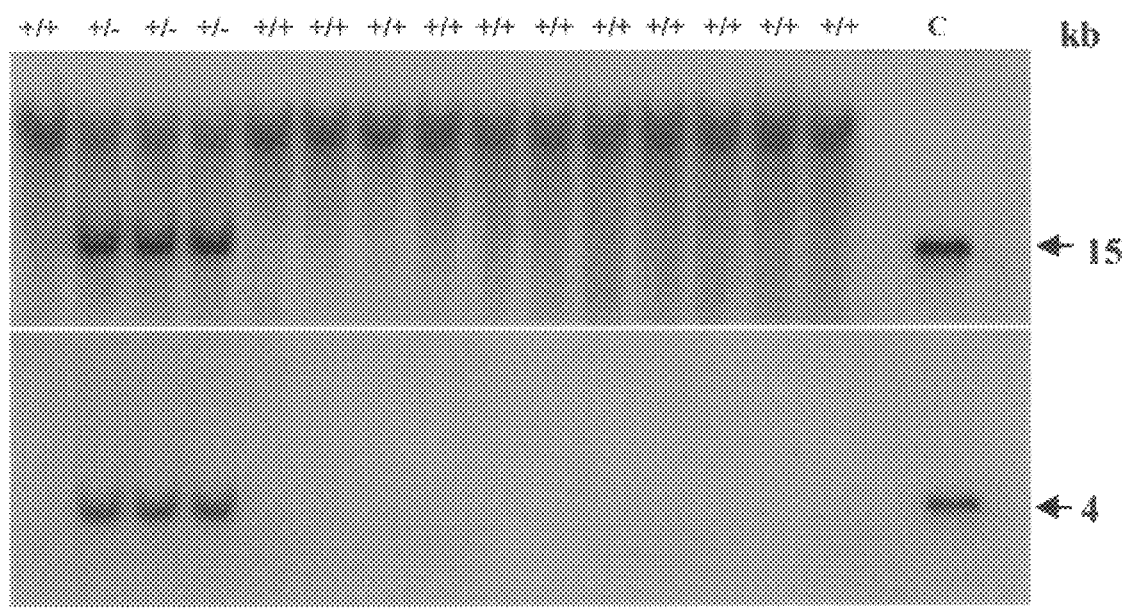
FIGURE 7

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 2034 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "DNA"

(xi) SEQUENCE DESCRIPTION: SEQ ID NO:1:

```
ATGGATCTTT GTCAGGTCTT CTTAACCTTG GCACTGGCAG TCACCAGCAG CACATTTTCT      60

GGAAGTGAGG CTACACCAGC TACTCTTGGC AAAGCTTCCC CAGTTCTGCA AAGAATCAAT     120

CCAAGCCTGG GGACAAGTTC TTCTGGAAAG CCTCGATTCA CCAAGTGTCG TTCCCCTGAA     180

CTGGAGACAT TTTCATGCTA CTGGACAGAA GGAGATAATC CTGATTTAAA GACCCCAGGA     240

TCTATTCAGC TGTACTATGC TAAAAGGGAA AGCCAACGAC AAGCTGCAAG AATTGCTCAT     300

GAATGGACCC AGGAATGGAA AGAATGCCCT GATTATGTCT CTGCTGGAAA AAACAGCTGT     360

TACTTCAACT CATCATATAC CTCCATTTGG ATACCCTACT GCATCAAGCT AACTACAAAT     420

GGTGATTTGC TGGACCAAAA ATGTTTCACT GTTGACGAAA TAGTGCAACC TGATCCACCC     480

ATTGGCCTCA ACTGGACTTT ACTAAACATT AGTTTGACCG GGATTCGTGG AGACATCCAA     540

GTGAGTTGGC AACCACCACC CAATGCAGAT GTTCTGAAGG GATGGATAAT TCTGGAGTAT     600

GAAATTCAGT ACAAAGAAGT AAATGAATCA AAATGGAAAG TGATGGGCCC TATATGGTTA     660

ACATACTGTC CAGTGTACTC ATTGAGAATG GATAAAGAAC ATGAAGTGCG GGTGAGATCC     720

AGACAACGGA GCTTTGAAAA GTACAGCGAG TTCAGCGAAG TCCTCCGTGT AATATTTCCT     780

CAGACGAACA TATTGGAAGC ATGTGAAGAA GATATCCAGT TTCCATGGTT CTTAATTATT     840
```

-continued

```
ATCTTTGGAA TATTTGGAGT AGCAGTCATG CTATTTGTAG TTATATTTTC AGGAACCAAG      900

TCCAATTCTC AGCACCCACA TCAAGAGATT GACAACCACC TGTATCACCA GCTTCAGAGG      960

ATCCGCCATC CCAAGCAGCA AAGGATTAAG ATGCTGATTT TACCCCCAGT CCCAGTTCCA     1020

AAGATTAAAG GGATTGATCC AGATCTTCTC AAGGAAGGGA AGTTGGAGGA GGTGAACACC     1080

ATCTTAGGCA TTCATGATAA CTACAAACCC GACTTCTACA ATGATGATTC CTGGGTCGAG     1140

TTCATTGAGC TAGATATTGA TGAAGCAGAT GTGGATGAGA AGACTGAAGG GTCTGACACA     1200

GACAGACTTC TAAGCAATGA TCATGAGAAA TCAGCTGGTA TCCTTGGAGC AAAGGATGAT     1260

GATTCTGGGC GTACCAGCTG TTACGACCCT GACATTTTGG ATACTGATTT CCATACCAGT     1320

GACATGTGTG ATGGTACCTT GAAGTTTCGT CAGTCACAGA AGTTAAATAT GGAAGCTGAT     1380

CTCTTGTGCC TTGATCAGAA GAATCTGAAG AACTTGCCTT ATGATGCTTC CCTTGGCTCT     1440

CTGCATCCCT CCATTACCCA GACAGTAGAA GAAAACAAGC CACAGCCACT TTTGAGCAGC     1500

GAAACTGAGG CAACCCACCA ACTCGCCTCT ACACCGATGA GTAATCCCAC ATCACTGGCA     1560

AACATTGACT TTTATGCCCA AGTAAGCGAC ATTACACCAG CAGGTGGTGA TGTCCTTTCC     1620

CCAGGCCAAA AGATTAAGGC AGGGATAGCC CAAGGCAATA CCCAGCGGGA GGTGGCCACG     1680

CCCTGCCAAG AAAATTACAG CATGAACAGT GCCTACTTTT GTGAGTCAGA TGCCAAAAAA     1740

TGCATCGCTG TGGCCCGTCG CATGGAAGCC ACGTCTTGTA TAAAACCAAG CTTTAACCAA     1800

GAGGACATTT ACATCACCAC AGAAAGCCTT ACCACTACTG CCCAGATGTC TGAGACAGCA     1860

GATATTGCTC CAGATGCTGA GATGTCTGTC CCAGACTACA CCACGGTTCA CACCGTGCAG     1920

TCTCCAAGGG GCCTTATACT CAACGCAACT GCTTTGCCTT TGCCTGACAA AAAGAATTTT     1980

CCCTCCTCGT GTGGTTATGT GAGCACAGAC CAACTGAACA AAATCATGCA GTAG          2034
```

(2) INFORMATION FOR SEQ ID NO:2:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:2:

```
CGATTCACCA AGTGTCGTTC CCCTGAACTG GAGACATTTT CATGC                       45
```

(2) INFORMATION FOR SEQ ID NO:3:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:3:

```
Arg Phe Thr Lys Cys Arg Ser Pro Glu Leu Glu Thr Phe Ser Cys
1               5                   10                  15
```

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: double (D) TOPOLOGY: linear (ii) MOLECULE TYPE: other nucleic acid
    (A) DESCRIPTION: /desc = "DNA"

(xi) SEQUENCE DESCRIPTION: SEQ ID NO:4:

ACAAGTTCTA AAAGGGAAAT AGTGCAAAAA GTGATGGGC           39

(2) INFORMATION FOR SEQ ID NO:5:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:5:

Thr Ser Ser Lys Arg Glu Ile Val Gln Lys Val Met Gly
1               5                   10

(2) INFORMATION FOR SEQ ID NO:6:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:6:

CGATTCACCT AGACTCGAGC AGTGTGGTTT TGCAAGAGGA AGCAA    45

(2) INFORMATION FOR SEQ ID NO:7:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:7:

Arg Phe Thr Thr Arg Ala Val Trp Phe Cys Lys Arg Lys Gln
1               5                   10

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:8:

ACAAGGAAAA AATAGTGCAA CAAGTGATGG GCC                 33

(2) INFORMATION FOR SEQ ID NO:9:

(i) SEQUENCE CHARACTERISTICS:
        (A) LENGTH: 9 amino acids
        (B) TYPE: amino acid (C) STRANDEDNESS: Not Relevant
        (D) TOPOLOGY: Not Relevant (ii) MOLECULE TYPE: protein (xi) SEQUENCE DESCRIPTION: SEQ ID NO:9:

Thr Arg Lys Lys Cys Asn Lys Trp Ala
1               5

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:10:

ACAATGCAAA AAGTGATGGG CGAAGATATC                                              30

(2) INFORMATION FOR SEQ ID NO:11:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:11:

Thr Met Gln Lys Val Met Gly Glu Asp Ile
1               5                   10

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:12:

ACAAATGGGA AGAAGATATC C                                                       21

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:13:

Thr Asn Gly Lys Lys Ile Ser
1               5

(2) INFORMATION FOR SEQ ID NO:14:

(i) SEQUENCE CHARACTERISTICS:
        (A) LENGTH: 23 base pairs (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:14:

CCAAGCTCCT ACAGAACATC CCA                                            23

(2) INFORMATION FOR SEQ ID NO:15:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:15:

ACATT GGGTGGAAAC AT                                                  22

(2) INFORMATION FOR SEQ ID NO:16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:16:

CCCCAGTTCT GCAAAGAATC                                                20

(2) INFORMATION FOR SEQ ID NO:17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:17:

ATCCA AATGGAGGTA                                                     20

(2) INFORMATION FOR SEQ ID NO:18:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:18:

CCTTCAGAAC ATCTGCATT                                                 19

(2) INFORMATION FOR SEQ ID NO:19:

(i) SEQUENCE CHARACTERISTICS:

```
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:19:

TGGAC TTGGTTCCTT CTTCACATGC TTCC                                         34
```

MICE MODELS OF GROWTH HORMONE INSENSITIVITY

FIELD OF THE INVENTION

The present invention relates to animal models of growth hormone insensitivity. In particular, the present invention relates to transgenic non-human mammals and methods for testing the usefulness of chemical compounds in the treatment of growth hormone insensitivity, growth hormone induced insulin resistence and diabetic end organ damage.

BACKGROUND OF THE INVENTION

Growth hormone (GH) is a protein hormone produced by the anterior pituitary. GH has multiple somatogenic and metabolic functions including promotion of skeletal growth and promotion of the differentiation of fat cells and chondrocytes. GH exerts its actions on many target tissues via binding to the growth hormone receptor (GHR). GH exerts many of its effects indirectly by stimulating the liver to produce insulin-like growth factor-I (IGF-I, also known as somatomedin C). GH may also stimulate IGF-I production in tissues other than the liver [Rechler et al. (1987) N. Engl. J. Med. 316:941]. IGF-I binds to IGF-I receptors on target cells in a variety of tissues and thereby regulates growth and differentiation (e.g., increased chondrogenesis leading to skeletal growth, increased protein synthesis and cell proliferation leading to an increase in extraskeletal growth). GH also exerts a direct effect by binding to the GHR in some tissues (e.g., stimulation of erythropoiesis) [Hughes and Friesen (1985) Ann. Rev. Physiol. 47:469 and Isaksson et al. (1985) Ann. Rev. Physiol. 47:483].

The GHR is a member of the cytokine/GH/prolactin receptor superfamily. Receptors in this superfamily transduce signals by association and activation of Janus tyrosine kinases (JAK kinases). In particular, the binding of GH to the GHR induces tyrosine phosphorylation and activation of JAK2 tyrosine kinase and tyrosine phosphorylation of the GHR [Xu et al. (1996) J. Biol. Chem. 271:19768 and Wang et al. (1996) Mol. Endocrinol. 10:1249]. GH binding to the GHR also induces tyrosine phosphorylation of cellular proteins termed signal transducers and activators of transcription (STATs), including STAT1, STAT3 and STAT5. GH has been shown to induce the association of STAT5 with the GHR in a GH-dependent manner; STAT5 is phosphorylated in response to GH binding and it is believed that JAK2 is the kinase that carries out this phosphorylation event. Two STAT5 homologs, STA5A and STAT5B have been identified in the mouse and STAT5A, but not STAT5B, undergoes GH-dependent tyrosine phosphorylation [Xu et al. (1996), supra]. These findings demonstrate that the GH-dependent activation of JAK-STAT pathways plays an important role in the GH signaling system that leads to GH-induced biological responses.

Circulating GH is complexed with one of two binding proteins, a high-affinity binding protein or a low affinity binding protein ($\alpha_2$-macroglobulin) [Baumann and Shaw (1990) J. Clin. Endocrinol. Metab. 70:680]. The high-affinity binding protein is termed growth hormone binding protein (GHBP). GHBP corresponds to the extracellular hormone-binding domain (i.e., the ectodomain) of the membrane associated GHR [Peeters and Friesen (1977) Endocrinol. 101:1 164; Baumann et al. (1986) J. Clin. Endocrinol. Metab. 62:134; Herington et al. (1986) J. Clin. Invest. 7:1817; Leung et al. (1987) Nature 330:537; Herington et al. (1986) Biochem. Biophys. Res. Commun. 139:150; Hocquette et al. (1990) Endocrinol. 127:1665 and Smith and Talamantes (1988) Endocrinol. 123:1489]. In humans and rabbits, GHBP is generated by proteolytic cleavage of the GHR to release the extracellular domain [Leung et al., supra; Trivedi et al. (1988) Endocrinol. 123:2201; and Sotiropoulos et al. (1993) Endocrinol. 132:1863]. In rodents, GHBP is generated by alternative splicing of an RNA transcript which also gives rise to mRNA encoding GHR [Smith et al. (1989) Mol. Endocrinol. 3:984 and Baumbach et al. (1989) Genes Devel. 3:1199]. GHBP is highly conserved through evolution. In addition, similar circulating ectodomains (i.e., extracellular domains of membrane-associated receptors) exist for several other receptors in the cytokine receptor family.

GHBP prolongs the half life of plasma growth hormone (GH) by effectively competing with GHR for ligand. By controlling free GH levels between secretory "peaks", GHBP appears to modulate the bioavailability of free GH. Given that GHBP and GHR are often co-expressed, serum GHBP levels have been extrapolated to estimate tissue concentrations of GHR [Baumann (1993) Proc. Soc. Exp. Biol. Med. 202:392 and (1994) J. Endocrinol. 141:1].

Plasma GHBP levels are altered in a variety of pathological states. In several conditions characterized by GH-resistance, GHBP levels are decreased (e.g., fetal life, senescence, malnutrition, insulin-dependent diabetes, hypothyroidism, liver cirrhosis, chronic renal failure, Laron syndrome, Pygmy dwarfism), whereas in overnutrition (obesity), GHBP levels are elevated [Baumann (1993), supra; Baumann (1994), supra; Baumann and Mercado (1993) Nutrition 9:547; and Maheshwari et al. (1996) J. Clin. Endocrinol. Metab. 81:995]. Extremely low or extremely elevated levels of GHBP can occur on a familial or genetic basis [Baumann et al. (1987) J. Clin. Endocrinol. Metab. 65:814; Daughaday and Trivedi (1987) Proc. Natl. Acad. Sci. USA 84:4636 and Rieu et al. (1993) J. Clin. Endocrinol. Metab. 76:857].

Laron syndrome, or GH insensitivity syndrome, is an example of mutations in the GHR gene resulting in absence or dysfunction of the GHR [Godowski et al. (1989) Proc. Natl. Acad. Sci. USA 86:8083; Berg et al. (1993) Am. J. Hum. Genetics 52:998; and Amelselem et al. (1993) Human Mol. Genetics 2:355]. When, as is the case in most families, the mutation is located in the extracellular domain of the GHR, affected patients also have absent, very low, or dysfunctional GHBP [Baumann et al. (1987), supra; Daughaday and Trivedi, supra; Rosenbloom et al. (1990) N. Engl. J. Med. 323:1367; and Savage et al. (1993) J. Clin. Endocrinol. Metab. 77:1465]. About 25 different mutations (partial gene deletions, nonsense and missense point mutations) have been described in various families [Berg et al. (1993), supra; Amelselem et al. (1993), supra; Woods et al. (1996) J. Clin. Endocrinol. Metab. 81:1686; Duquesnoy et al. (1994) EMBO J. 13:1386; Kou et al (1993) J. Clin. Endocrinol. Metab. 76:54; Ayling et al. (1996) Progr. 10th Internatl. Congr. Endocrinol., 748; and Goddard et al (1995) N. Engl. J. Med. 333:1073].

Patients with Laron syndrome are characterized by a severe postnatal growth failure and markedly reduced adult height. In addition, clinical findings in patients with Laron syndrome include obesity, normal to high levels of circulating GH, low levels of IGF-1, low or no GHBP, resistance to exogenous GH treatment and hypoglycemia [Savage et al. 1993, supra; Rosenfeld et al. (1994) Endo Rev. 15:369]. Currently, the only form of treatment for Laron syndrome is infusion of recombinant human IGF-1 [Walker et al. (1991) N. Engl. J. Med. 324:1483]. No mammalian models for this disorder are available for the development of alternative therapeutic modalities.

The art needs a mammalian animal model of Laron syndrome to provide a model system for the screening of therapeutic compounds and regimens to provide improved therapy for patients suffering from GH insensitivity syndrome (i.e., Laron's syndrome).

SUMMARY OF THE INVENTION

The present invention provides mammalian models for GH insensitivity syndrome including Laron syndrome. These mammalian models further provide a means for screening compounds for growth promoting activity. Accordingly, the present invention provides a non-human mammal expressing reduced levels of growth hormone receptor. In a preferred embodiment, the mammal lacks the ability to produce functional growth hormone receptor. In another embodiment the invention provides a non-human mammal expressing reduced levels of growth hormone binding protein. In a preferred embodiment, the mammal lacks the ability to produce functional growth hormone binding protein. In another embodiment, the present invention provides a non-human mammal expressing reduced levels of growth hormone receptor and reduced levels of growth hormone binding protein. In a preferred embodiment, the non-human mammal expressing reduced levels of growth hormone receptor lacks the ability to produce functional growth hormone binding protein. In yet another preferred embodiment, the non-human mammal expressing reduced levels of growth hormone receptor also produces reduced levels of insulin-like growth factor-I.

The present invention is not limited by the nature of the non-human mammal employed. In a preferred embodiment, the non-human mammal is selected from the order Rodentia. In a particularly preferred embodiment, the non-human mammal is a mouse.

The present invention is not limited by the means employed to render the non-human mammal capable of expressing only reduced levels of growth hormone receptor. In a preferred embodiment, the genome of the non-human mammal, preferably a mouse, contains a heterologous polynucleotide sequence inserted into the endogenous growth hormone receptor gene. The present invention is not limited by the nature of the heterologous polynucleotide sequence employed to disrupt the endogenous growth hormone receptor gene. Any heterologous polynucleotide sequence capable of disrupting the endogenous growth hormone receptor gene (e.g., by introducing a premature stop codon, causing a frameshift mutation, disrupting proper splicing, etc.). In a preferred embodiment, the heterologous polynucleotide sequence comprises the neo gene.

The present invention also provides a method for screening compounds for growth promoting activity, comprising: a) providing: i) a non-human mammal expressing reduced levels of growth hormone receptor; ii) a composition comprising a test compound in a form suitable for administration to the mammal; and b) administering the test compound to the mammal. In a preferred embodiment, the method further comprises c) measuring an increase in the growth rate of the mammal and thereby identifying a compound as having growth promoting activity. The invention is not limited by the nature of the test compound employed. In a preferred embodiment, the test compound is selected from the group consisting of compounds that modulate or activate molecules involved in the transduction of the signals associated with the binding of GH to the GHR, such as molecules within the JAK/STAT pathway (e.g., JAK2 kinase, STATS, STAT1, etc.).

The screening method of the present invention is not limited by nature of defect which renders the mammal capable of expressing only a reduced level of growth hormone receptor. In a preferred embodiment, the genome of the non-human mammal contains a disruption in the endogenous growth hormone receptor gene. In another preferred embodiment, the mammal expressing reduced levels of growth hormone receptor lacks the ability to produce functional growth hormone receptor. In yet another preferred embodiment, the mammal expressing reduced levels of growth hormone receptor further expresses reduced levels of growth hormone binding protein and most preferably lacks the ability to produce functional growth hormone binding protein.

The present invention further provides a method for disrupting a growth hormone receptor gene in a cell, comprising: a) providing a first oligonucleotide having a sequence comprising: i) at least a portion of a non-human growth hormone receptor gene; and ii) a second oligonucleotide capable of disrupting the non-human growth hormone receptor gene; and b) introducing the first oligonucleotide into a non-human cell under conditions such that the first oligonucleotide is homologously recombined into at least one of the naturally occurring growth hormone receptor genes in the genome of said cell to produce a cell containing at least one disrupted growth hormone receptor allele.

The method is not limited by the nature of the second oligonucleotide used to disrupt the non-human growth hormone receptor gene. Any oligonucleotide sequence capable of disrupting the endogenous growth hormone receptor gene (e.g., by introducing a premature stop codon, causing a frameshift mutation, disrupting proper splicing, etc.) may be employed. In a preferred embodiment, the second oligonucleotide comprises a positive selectable marker gene. In a particularly preferred embodiment, the second oligonucleotide comprises the neo gene.

In a preferred embodiment, the cell employed in the method is an embryonic stem cell, preferably an embryonic stem cell from a mammal within the order Rodentia and most preferably a mouse embryonic stem cell.

In a preferred embodiment, the method further comprises injecting the embryonic stem cell containing at least one disrupted growth hormone receptor allele into the blastocyst of a non-human animal. In another preferred embodiment, the method further comprises introducing the injected blastocyst into a pseudo-pregnant non-human animal and permitting the pseudo-pregnant animal to deliver progeny containing the homologously recombined oligonucleotide. Thus, in a preferred embodiment, the method for disrupting a growth hormone receptor gene in a cell is a method for producing a non-human transgenic animal containing at least one disrupted growth hormone receptor allele. In another preferred embodiment, the progeny containing the homologously recombined oligonucleotide is further characterized by expressing reduced levels of growth hormone receptor. In a particularly preferred embodiment, the progeny lacks the ability to produce functional growth hormone receptor. In another preferred embodiment, the progeny is further characterized by expressing reduced levels of growth hormone binding protein and most preferably the progeny lacks the ability to produce functional growth hormone binding protein.

The invention further provides a method comprising: a) providing a non-human mammal whose genome contains two disrupted alleles of a first growth hormone receptor gene and b) administering a diabetogenic compound (e.g., streptozotocin) to the mammal to induce a diabetic state in the mammal. While not limiting the present invention to any particular mechanism, the administration of a diabetogenic compound to these mammals may cause kidney lesions; kidney lesions that develop are expected to be due to the presence of a second growth hormone receptor in these mammals. This method offers an opportunity to identify and isolate the second growth hormone receptor which may represent a kidney-specific growth hormone receptor. To isolate the second growth hormone receptor, membrane protein preparations (e.g., from kidney) from the mammal whose genome contains two disrupted alleles of a first growth hormone receptor gene (i.e., these mammals lack the ability to express the first growth hormone receptor) are prepared using standard techniques and applied to a chromatographic resin comprising growth hormone (i.e., a growth hormone affinity resin). The second growth hormone receptor would bind to the resin and after washing the resin, the second receptor is eluted to yield a purified preparation of the second growth hormone receptor. The availability of a purified preparation of the second growth hormone receptor permits the generation of antibodies specific to this second receptor, permits the amino acid sequence of the second receptor to be determined thereby allowing the design of oligonucleotides suitable for the identification of the gene encoding the second receptor. Identification of s second growth hormone receptor further permits the identification of compounds that interact with this second receptor (e.g., agonists, antagonists, mimetics, etc.).

DESCRIPTION OF THE DRAWINGS

FIGS. 3A–G provide schematic representations of the targeted disruption of the GHR/BP gene. FIG. 3A depicts the possible pre-mRNA splicing of the disrupted GHR/BP gene. FIG. 3B shows the normal nucleotide (SEQ ID NO:2) and amino acid (SEQ ID NO:3) sequences encoded by the region around the DraIII site in exon 4 which was used for the insertion of the neo gene. FIG. 3C shows the nucleotide (SEQ ID NO:4) and amino acid (SEQ ID NO:5) sequences at the junction sites for the spliced wild-type GHR/BP mRNA. FIGS. 3D–G show the nucleotide (SEQ ID NOS:6, 8, 10 and 12) and amino acid (SEQ ID NOS:7, 9, 11 and 13) sequences at the splicing sites of the four possible splicing patterns (I–IV) predicted in FIG. 3A.

FIGS. 7A–B show autoradiograms of Southern blots generated using genomic DNA isolated from GHRIBP+/− mice.

DEFINITIONS

Figure 1A:
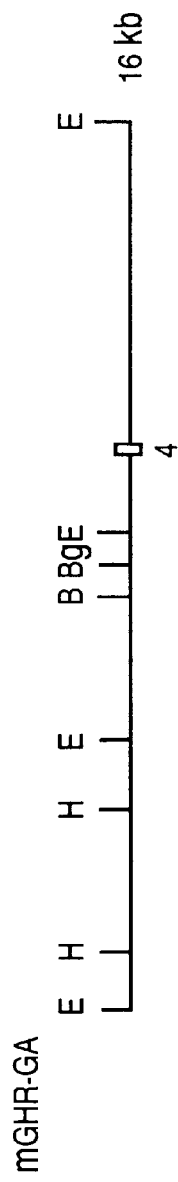
FIG. 1A provides a schematic of the insert contained within the genomic clone mGHR-GA.

To facilitate understanding of the invention, a number of terms are defined below.

The "non-human animals" of the invention comprise any non-human animal whose genome contains a polynucleotide sequence (e.g., a gene) encoding a modified form of the growth hormone receptor/binding protein (GHR/BP) gene. The modification may reduce or prevent the expression of GHR, GHBP or both or may render the resulting GHR or GHBP completely nonfunctional. Such non-human animals include vertebrates, preferably mammals such as rodents, non-human primates, ovines, bovines, ruminants, lagomorphs, porcines, caprines, equines, canines, felines, aves, etc. Preferred non-human animals are selected from the order Rodentia which includes murines (e.g., rats and mice), most preferably mice.

A "non-human mammal expressing reduced levels of growth hormone receptor" is a mammal which expresses a level of GHR which is lower than that found in a wild-type mammal. For example, the invention provides transgenic mice containing a disruption in one allele of the GHR/BP gene (i.e., heterozygous or GHR/BP+/− mice) which produce about ½ the level of GHR as compared to the level produced in wild-type (i.e., mice lacking a modified or disrupted GHR/BP allele) or GHR/BP+/+ mice. The level of GHR produced in a mammal may be determined by a variety methods including Western blot analysis of protein extracted from the liver as described in Ex. 4. A mammal that "lacks the ability to produce functional growth hormone receptor" is a mammal that produces undetectable levels of functional GHR (e.g., by Western blot analysis). A functional GHR is a GHR which retains the biological activity of the wild-type GHR and which preferably is of the same molecular weight as the wild-type GHR.

A "non-human mammal expressing reduced levels of growth hormone binding protein" is a mammal which expresses a level of GHBP which is lower than that found in a wild-type mammal. For example, the invention provides transgenic mice containing a disruption in one allele of the GHR/BP gene (i.e., heterozygous or GHR/BP+/− mice)

which produce about ½ the level of GHBP in the serum as compared to the level produced in the serum of wild-type (i.e., mice lacking a modified or disrupted GHR/BP allele) or GHR/BP+/+ mice. The level of serum GHBP produced in a mammal may be determined by a variety of methods including the assay described in Ex. 4. A mammal that "lacks the ability to produce functional growth hormone binding protein" is a mammal that produces undetectable levels of GHBP (i.e., a level which is not statistically above background levels in the assay employed). A functional GHBP is a GHBP which has the same properties as does the wild-type GHBP including molecular weight.

A "non-human mammal expressing reduced levels of insulin-like growth factor-I" is a mammal which expresses a level of IGF-I in the serum which is lower than that found in a wild-type mammal. For example, the invention provides transgenic mice containing a disruption in both alleles of the GHR/BP gene (i.e., homozygous or GHR/BP−/− mice) which produce about 1/10 the level of serum IGF-I as compared to the level produced in wild-type (i.e., mice lacking a modified or disrupted GHR/BP allele) or GHR/BP+/+ mice. The level of IGF-I produced in a mammal may be determined by a variety methods including the radioimmunoassay described in Ex. 4.

The "non-human animals having a genetically engineered genotype" of the invention are preferably produced by experimental manipulation of the genome of the germline of the non-human animal. These genetically engineered non-human animals may be produced by several methods including the introduction of a "transgene" comprising nucleic acid (usually DNA) into an embryonal target cell or integration into a chromosome of the somatic and/or germ line cells of a non-human animal by way of human intervention, such as by the methods described herein. Non-human animals which contain a transgene are referred to as "transgenic non-human animals". A transgenic animal is an animal whose genome has been altered by the introduction of a transgene. As used herein the term "transgenic animal" encompasses knockout animals [i.e., animals containing one or more disrupted alleles of a gene(s)].

The term "transgene" as used herein refers to a foreign gene that is placed into an organism by introducing the foreign gene into embryonic stem (ES) cells, newly fertilized eggs or early embryos. The term "foreign gene" refers to any nucleic acid (e.g., gene sequence) which is introduced into the genome of an animal by experimental manipulations and may include gene sequences found in that animal so long as the introduced gene contains some modification (e.g., a point mutation, the presence of a selectable marker gene, the presence of a loxP site, etc.) relative to the naturally-occurring gene.

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) are retained. The term "gene" encompasses both genomic and cDNA forms of a gene. A gene may further comprise endogenous (i.e., naturally associated with a given gene) or heterologous control signals such as promoters, enhancers, termination and/or polyadenylation signals.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The terms "targeting vector" or "targeting construct" refer to polynucleotide sequences comprising a selectable marker gene flanked on either side by GHR/BP gene sequences. The targeting vector contains GHR/BP gene sequences sufficient to permit the homologous recombination of the targeting vector into at least one allele of the GHR/BP gene resident in the chromosomes of the target or recipient cell (e.g., ES cells). Typically, the targeting vector will contain approximately 5 to 15 kb of DNA homologous to the GHR/BP gene (more than 15 kb or less than 5 kb of the GHR/BP gene sequences may be employed so long as the amount employed is sufficient to permit homologous recombination into the GHR/BP gene); this 5 to 15 kb of DNA is divided on each side of the selectable marker gene. The targeting vector may contain more than one selectable maker gene. When more than one selectable marker gene is employed, the targeting vector preferably contains a positive selectable marker (e.g., the neo gene) and a negative selectable marker [e.g., the Herpes simplex virus tk (HSV-tk) gene]. The presence of the positive selectable marker permits the selection of recipient cells containing an integrated copy of the targeting vector whether this integration occurred at the target site or at a random site. The presence of the negative selectable marker permits the identification of recipient cells containing the targeting vector at the targeted site (i.e., which has integrated by virtue of homologous recombination into the target site); cells which survive when grown in medium which selects against the expression of the negative selectable marker do not contain a copy of the negative selectable marker.

The targeting vectors of the present invention are of the "replacement-type;" integration of a replacement-type vector results in the insertion of a selectable marker into the target gene. As demonstrated herein replacement-type targeting vectors may be employed to disrupt a gene resulting in the generation of a null allele (i.e., an allele incapable of expressing a functional protein; null alleles may be generated by deleting a portion of the coding region, deleting the entire gene, introducing an insertion and/or a frameshift mutation, etc.) or may be used to introduce a modification (e.g., one or more point mutations) into a gene.

The terms "selectable marker" or "selectable gene product" as used herein refer to the use of a gene which encodes an enzymatic activity that confers resistance to an antibiotic or drug upon the cell in which the selectable marker is expressed. Selectable markers may be "positive"; positive selectable markers typically are dominant selectable markers, i.e., genes which encode an enzymatic activity which can be detected in any mammalian cell or cell line (including ES cells). Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Selectable markers may be "negative"; negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "promoter element" or "promoter" as used herein refer to a DNA sequence that is located at the 5' end of (i.e., precedes) a gene in a DNA polymer and provides a site for initiation of the transcription of the gene into mRNA.

The term "an oligonucleotide sequence comprising at least a portion of a non-human GHR/BP gene" refers to a polynucleotide sequence (i.e., a nucleic acid sequence) containing a nucleotide sequence derived from a non-human GHR/BP gene. This sequence may encode a portion (including the entire) of the GHR and/or GHBP proteins; alternatively, this sequence may contain non-coding regions derived from the GHR/BP gene or a combination of coding and non-coding regions. The oligonucleotide may be RNA or DNA and may be of genomic or synthetic origin.

As used herein the term "portion" when in reference to a gene refers to fragments of that gene. The fragments may range in size from about 17 nucleotides to the entire gene sequence minus one nucleotide. Thus, "an oligonucleotide comprising at least a portion of a gene" may comprise fragments of the gene or the entire gene.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

The transgenic animals of the present invention are preferentially generated by introduction of the targeting vectors into embryonal stem (ES) cells. ES cells are obtained by culturing pre-implantation embryos in vitro under appropriate conditions [Evans, et al. (1981) Nature 292:154–156; Bradley, et al. (1984) Nature 309:255–258; Gossler, et al. (1986) Proc. Acad. Sci. USA 83:9065–9069; and Robertson, et al. (1986) Nature 322:445–448]. Transgenes can be efficiently introduced into the ES cells by DNA transfection using a variety of methods known to the art including electroporation, calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal. For review, see Jaenisch (1988) Science 240:1468–1474. Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells which have integrated the transgene. This technique obviates the need for growth of the transfected ES cells under appropriate selective conditions prior to transfer into the blastocoel.

Alternative methods for the generation of transgenic animals containing an altered GHR/BP gene are known to the art. For example, embryonal cells at various developmental stages can be used to introduce transgenes for the production of transgenic animals. Different methods are used depending on the stage of development of the embryonal cell. The zygote, particularly at the pronuclei stage (i.e., prior to fusion of the male and female pronuclei), is a preferred target for micro-injection. In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage [Brinster, et al. (1985) Proc. Natl. Acad. Sci. USA 82:4438–4442]. As a consequence, all cells of the transgenic non-human animal will carry the incorporated transgene. This will in general also be reflected in the efficient transmission of the transgene to offspring of the founder since 50% of the germ cells will harbor the transgene. Micro-injection of zygotes is the preferred method for incorporating transgenes in practicing the invention. U.S. Pat. No. 4,873191 describes a method for the micro-injection of zygotes; the disclosure of this patent is incorporated herein in its entirety.

Retroviral infection can also be used to introduce transgenes into a non-human animal. The developing non-human embryo can be cultured in vitro to the blastocyst stage. During this time, the blastomeres can be targets for retroviral infection [Janenich (1976) Proc. Natl. Acad. Sci. USA 73:1260–1264]. Efficient infection of the blastomeres is obtained by enzymatic treatment to remove the zona pellucida [Hogan et al. (1986) in Manipulating the Mouse Embryo, Cold Spring Harbor Laboratory Press, Plainview, N.Y.]. The viral vector system used to introduce the transgene is typically a replication-defective retrovirus carrying the transgene [Jahner, D. et al. (1985) Proc. Natl. Acad Sci. USA 82:6927–6931; Van der Putten, et al. (1985) Proc. Natl. Acad Sci. USA 82:6148–6152]. Transfection is easily and efficiently obtained by culturing the blastomeres on a monolayer of virus-producing cells [Van der Putten, supra; Stewart, et al. (1987) EMBO J. 6:383–388]. Alternatively, infection can be performed at a later stage. Virus or virus-producing cells can be injected into the blastocoele [Jahner, D. et al. (1982) Nature 298:623–628]. Most of the founders will be mosaic for the transgene since incorporation occurs only in a subset of cells which form the transgenic animal. Further, the founder may contain various retroviral insertions of the transgene at different positions in the genome which generally will segregate in the offspring. In addition, it is also possible to introduce transgenes into the germline, albeit with low efficiency, by intrauterine retroviral infection of the midgestation embryo [Jahner, D. et al. (1982) supra]. Additional means of using retroviruses or retroviral vectors to create transgenic animals known to the art involves the micro-injection of retroviral particles or mitomycin C-treated cells producing retrovirus into the perivitelline space of fertilized eggs or early embryos [PCT International Application WO 90/08832 (1990) and Haskell and Bowen (1995) Mol. Reprod. Dev. 40:386].

As used herein, the term "polymerase chain reaction" ("PCR") refers to the method of K. B. Mullis disclosed in U.S. Pat. Nos. 4,683,195, 4,683,202 and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., visualization of DNA by ethidum bromide staining following electrophoresis on agarose or acrylamide gels; hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

The term "order Rodentia" refers to rodents i.e., placental mammals (class Euthria) which include the family Muridae (rats and mice).

An animal whose genome "comprises a heterologous polynucleotide sequence inserted into the endogenous growth hormone receptor gene" is an animal whose genome contains a polynucleotide sequence not naturally found in the endogenous GHR/BP gene. The heterologous polynucleotide sequence may comprise a selectable marker gene not naturally found in the GHR/BP gene which is introduced by means of molecular biological methods. The heterologous selectable marker may be either a positive selectable marker or a negative or counter-selectable marker.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention. In other words, a known therapeutic compound is not limited to a compound efficacious in the treatment of GH insensitivity in animals (e.g., human Laron syndrome).

A compound is said to be "in a form suitable for administration to the mammal" when the compound may be administered to a mammal by any desired route (e.g., oral, intravenous, subcutaneous, intramuscular, etc.) and the compound or its active metabolites appears in the blood of the mammal. Administration of a compound to a pregnant female may result in delivery of the compound to the fetuses of the pregnant animal.

A compound is said to have "growth promoting activity" if administration of the compound to an animal having reduced levels of GHR results is increasing the growth rate of these animals. A test compound may be examined for its growth promoting activity by administration of the test compound to an animal such as a GHR/BP-/- mouse followed by measurement of the growth rate of the treated animal or another clinical endpoint such as an increase in IGF-I levels; a compound which increases the growth rate of the GHR/BP-/- mouse relative to control animals (i.e., untreated GHR/BP-/- mice) is said to have growth promoting activity.

DESCRIPTION OF THE INVENTION

The present invention relates to transgenic models of Laron's syndrome and, more particularly, to transgenic non-human animals and methods for testing the usefulness of chemical compounds in the treatment of Laron's syndrome or other disorders associated with insensitivity to GH. The description of the invention is divided into the following parts: I) The Organization of the Human and Mouse GHR/BP Genes; II) Human Disorders Associated With Alterations In The GHR/BP Gene; III) Animal Models for GH Insensitivity; IV) Human Disease Associated With Perturbations In GH Expression and V) Screening Potential Therapeutic Compounds.

I. The Organization Of The Human And Mouse GHR/BP Genes

Genomic and cDNA clones encoding human GHR/BP (hGHR/BP) and mouse GHR/BP (mGHR/BP) have been isolated [Godowski et al. (1989) Proc. Natl. Acad. Sci. USA 86:8083; Leung et al. (1987), supla; Zhou et al. (1994) Receptor 4:223; Smith et al. (1989) Mol. Endocrinol. 3:984]. The hGHR/BP gene contains at least 10 exons; 9 of these exons encode protein (exons 2–10). Exon 1 comprises 5' untranslated sequences; exon 2 encodes primarily the signal peptide; exons 3–7 encode the extracellular domain of the receptor. The transmembrane portion of the human receptor is encoded by exon 8 and the intracellular region of the receptor is encoded by exons 9 and 10. The hGHBP is thought to be generated by proteolytic processing of the hGHR which yields the extracellular, ligand binding domain of the receptor. In rabbits and pigs, GHBPs are also generated from full-length GHR by proteolytic cleavage.

In mice and rats, the GHBP is produced through alternative splicing of a common GHR/BP pre-mRNA [Smith et al. (1989), supra and Baumbach et al. (1989) Genes Dev.

3:1199; and Zhou et al. (1994), supra and (1996) Gene 177:257]. In rodents, the difference between GHR and GHBP is that the GHBP possesses a hydrophilic tail at the carboxyl terminus which replaces the transmembrane and intracellular domains of the full-length GHR [Smith et al. (1989), supra and Baumbach et al. (1989), supra].

Two distinct mRNAs are found in mouse tissues and cells which express mGHR, i.e. one encoding the mGHR and one encoding the mGHBP [Smith et al. (1989) Mol. Endocrinol. 3:9841. The mGHBP RNA contains exons 2–7 of the mGHR gene and sequences encoding an additional 27 amino acids at the carboxy terminus. These C-terminal amino acids are encoded by an exon, termed exon 8A, which is located between exons 7 and 8 of the mGHR/BP gene [Zhou et al. (1994) Receptor 4:223 and Smith et al. (1989), supra]. Exon 8A possesses an 81 bp 3' untranslated region that contains two tandem and overlapping poly A addition sequences (AAUAA) starting 54 bp downstream from the translational stop codon as well as a rather large AT rich segment in this area. Located between exon 7 and 8A is an intron which possesses the canonical precursor mRNA 5'-splice donor and 3'-splice acceptor sequences. Located between exons 8A and 8 is a 1600 bp GHBP 3' flanking region. This sequence encodes the 3' portion of the mGHR intron between exons 7 and 8 and contains the 3'-splice acceptor site.

The intron between the mGHR exon 7 and 8 is herein referred to as intron 7/8. This intron is removed in the production of mGHR mRNA. Located within intron 7/8 is the mGHBP exon 8A. The intron between the mGHBP exons 7 and 8A is herein referred to as intron 7/8A. This intron contains 287 bases which are removed in generating mGHBP mRNA. Also, for clarity, herein the mGHR and mGHBP are referred to as being encoded by separate genes. However, it is noted that the 5' portions (exons 2–7) of each of the molecules is identical, and thus the mGHBP "gene" is embedded in the mGHR gene.

The rat analog of the mouse exon 8A is found in a similar location in the rat GHR/BP gene [Zhou et al. (1996), supra]. The hGHR/BP gene does not contain an analog of exon 8A [Godowski et al. (1989), supra].

In the mouse, the GHR mRNA also contains exons 2–7 and, in addition, contains exons 8–10. Exon 8 encodes the transmembrane portion of the mGHR and exons 9–10 encode the intracellular domain of the mGHR.

The GHR/BP gene is expressed in almost all tissues in mammals [Herington et al. (1991) Acta Endocrinol. 124:14] and all stages of development, including early embryonic stages [Nicoll et al. (1991) Growth Regul. 1:133; Walker et al. (1992) Pediatric Res. 31:335; and Garcia-Aragon et al. (1992) Development 114:869]. It is well known that GH through the GHR promotes body growth of postnatal infants and changes the metabolic status of both newborns and adults.

II. Human Disorders Associated With Alterations In The GHR/BP Gene

Laron syndrome is a form of dwarfism characterized by high levels of GH and low levels of IGF-I in the circulation; this disorder is an autosomal recessive hereditary disease resulting from a polymorphic molecular defect in the human GHR. Mutations of the GHR/BP gene have been demonstrated in patients with Laron syndrome [Godowski et al. (1989), supra; Amselem el al. (1989), supra; Duquesnoy et al. (1991); Edery el al. (1993); Duquesnoy et al. (1994); Kou et al. (1993), supra; and Berg et al. (1992), supra]. These mutations result in the production of non-functional GHR and/or GHBP. A number of these mutations are found in exon 4 of the human GHR/BP gene. Other mutations effect the splicing of the GHR/BP RNA including a splice site mutation in exon 8 which abolishes the transmembrane helix and severely truncates the intracellular domain [Woods et al. (1996), supra]. This results in elevated GHBP levels and GH resistance, presumably due to a lack of intracellular signaling. Another mutation involves the carboxy-terminal part of the GHBP (a region adjacent to the transmembrane domain of the GHR) and prevents GHR dimer stabilization via direct GHR-GHR contact [Duquesnoy et al. (1994), supra]. In this mutant GHR/GHBP, GH binding is normal but the G1R fails to properly dimerize and transduce a biological signal. Mutations in the intracellular domain of the GHR include two non-contiguous base substitutions in the same patient [Kou et al. (1993), supra], and a dominant negative mutation in the proline-rich region [Ayling et al. (1996), supra]. More "subtle" mutations in the GHR result in a milder phenotype with short stature and moderately decreased GHBP levels [Goddard et al. (1995), supra].

Patients with Laron syndrome have some of the same clinical findings as those seen in patients with severe isolated GH deficiency (e.g., severe growth retardation, obesity and low serum IGF-I levels). However, in contrast to patients with GH deficiency, patients with Laron syndrome have high GH levels and fail to respond to GH treatment by increasing IGF-I levels and growth.

In a study of 27 patients with Laron syndrome, the following clinical features and endocrinological findings were made: birth weights and lengths were below average (median birth weight: −0.72 SDS; median birth length: −1.59); median height was −6.1 SDS (standard deviation scores) (range: −3.8 to −10.2); skeletal maturation was delayed in the majority of patients; percentage weight for height was above average (median: 111.3); hypoglycemia was documented in ⅓ of the patients; serum basal GH levels were normal or elevated (median value: 15.9 $\mu$g/L); IGF-I values were generally less than 0.1 percentile for age, IGF-II values were less than 5th percentile for age; IGFBP-1 levels were normal to elevated; IGFBP-2 levels were normal; IGFBP-3 values were less than 5th percentile for age; GHBP was undetectable in the majority of patients (18/27), extremely low in 2/27 patients and normal in 7/27 patients and production of IGF-I in response to hGH was less than 0.1 percentile for age [Savage et al. (1993), supra].

The only form of treatment currently available for Laron syndrome is administration of IGF-I. IGF-I has been administered both by periodic subcutaneous injection and constant infusion [Laron et al. (1988) Lancet 2:1170 and Proceedings and abstracts of the 72nd annual meeting of the Endocrine Society, 1990, Endocrine Society:75, abstract and Walker et al. (1991), supra]. Constant infusion of rIGF-I over an 11 day period resulted in a GH-like anabolic response: decreased serum and urine urea nitrogen, increase in urinary calcium excretion, decrease in urinary excretion of phosphate and sodium. GH levels were reduced during IGF-I administration. A reduction of fasting blood glucose levels was observed during administration of IGF-I, a well recognized effect of IGF-I [Guler et al. (1989) Proc. Natl. Acad. Sci. USA 86:2868; Laron et al. (1988), supra and Guler et al. (1987) N. Engl. J. Med. 317:137]. Postprandial hyperglycemia was observed in this patient during the administration of IGF-I which resulted primarily from the suppression of insulin secretion [Walker et al. (1991), supra]. All responses returned to their formal abnormal levels rapidly after cessation of treatment; therefore, IGF-I therapy requires chronic infusion to achieve therapeutic effects.

III. Animal Models For GH Insensitivity

The present invention provides the first non-human mammalian model of Laron syndrome. A non-mammalian model, the sex-linked dwarf chicken, has been described [Burnside et al. (1992) Gen. Com. Endocrinol. 88:20 and (1991) Endocrinol. 128:3183]. As the physiology of birds is less similar to humans than is that of non-human mammals and further the dwarfism is sex-linked in the chicken model while it is not in humans, the chicken provides a suboptimal model for Laron syndrome. In addition, chickens are fairly large animals which are more expensive to maintain as compared to small mammals such as mice.

The present invention provides transgenic animal models of GH insensitivity. Importantly, the present invention provides for the first time a mammalian model of GH insensitivity (e.g., Laron syndrome). These models are exemplified using transgenic mice which contain targeted disruptions of the GHR/BP gene. These animals, termed "knockout" animals, lack the ability to express either GHR ("GHR knockouts"), GHBP ("GHBP knockouts") or both ("GHR/BP knockouts"). These transgenic mice are preferably generated using homologous recombination in embryonic stem (ES) cells; however, equivalent transgenic mice can also be produced by microinjection of mammalian oocytes. Techniques for the isolation, culture, microinjection and implantation of a variety of mammalian oocytes (e.g., mouse, pig, sheep, cow, etc.) are known to the art.

In order to produce the transgenic mice of the present invention, cloned mouse GHR/BP gene sequences are used to either disrupt the GHR/BP gene in such a manner that either 1) GHR and GHBP cannot be produced, 2) GHR cannot be produced or GHBP cannot be produced.

a. GHR/BP Gene Disrupted Mice

Mice lacking the ability to produce both GHR and GHBP were generated using the technique of homologous recombination in ES cells. A targeting vector containing large fragments of GHR/BP genomic sequences flanking a selectable marker gene was inserted into the genome in ES cells via homologous recombination. This recombination event resulted in the deletion of the majority of exon 4 and the insertion of the neo gene. Exon 4 was chosen as the site for disruption of the GHR/BP gene as in Laron syndrome, several mutations have been mapped to exon 4 in the human GHR/BP gene. However, the present invention is not limited to the disruption of the GHR/BP in exon 4 for the production of GHR/BP knockout mice. Any site within the GHR/BP may be employed as the target for disruption provided that alteration of that site prevents the expression of functional GHR and GHBP.

ES cells containing the homologously recombined targeting vector were injected into blastocysts and chimeric mice derived from the injected blastocysts were mated to produce mice heterozygous for the disrupted GHR/BP gene. Heterozygous mice were then intercrossed to generate homozygous GHR/BP null progeny (homozygous GHR/BP knockouts). The inability to produce functional GHR and GHBP results in mice which are about 40–50% smaller than their non-transgenic litter mates. The homozygous GHR/BP knockout mice display clinical findings which closely parallel those seen in humans with Laron syndrome (i.e., dwarfism, low IGF-I levels, elevated GH levels, undetectable GHBP). Thus, homozygous GHR/BP knockout mice provide a mammalian model for GH insensitivity including Laron syndrome.

GHR/BP knockout mice may be produced by a variety of means. It is not required that the specific targeting vector employed herein be used. Any targeting vector containing a fragment of mouse GHR/BP genomic sequence which is capable of homologously recombining into the mouse GHR/BP gene in a manner that disrupts the GHR/BP gene (e.g., introduction of a frameshift, premature stop codon, missense mutation, etc.) may be employed. The targeting vector may be of the replacement- or insertion-type [Huang (1993) Lab. Animal Sci. 43:156]. Replacement-type vectors contain two regions of homology with the targeted gene flanking a selectable marker and result in the insertion of the selectable marker which thereby disrupts the targeted gene. Insertion-type vectors contain a single region of homology with the targeted gene and result in the insertion of the entire targeting vector into the targeted gene.

The generation of GHR/BP gene disrupted (i.e., knockout) mice need not employ ES cells; targeting vectors or transgenes may be microinjected into mouse oocytes to generate mice containing a disrupted GHR/BP gene. The targeting vector employed need not employ a selectable marker, although the use of a selectable marker is preferred. PCR can be employed to screen the targeted cells to identify cells containing a disrupted GHR/BP gene without the need to use a selectable marker and subject the targeted cells to growth in selective medium. In addition, chimeric RNA-DNA oligonucleotides containing modified RNA residues (2'-O-methyl modification of the ribose) can be used to target mutations (e.g., the introduction of a frameshift, premature stop codon, etc.) into the GHR/BP gene using ES cells or oocytes to create GHR/BP knockout mice [Strauss el al. (1996) Science 273:1386].

Mice containing a disrupted GHR/BP gene find a number of uses. As discussed in more detail below, homozygous GHR/BP knockout mice provide a means for screening compounds beneficial for the treatment of Laron syndrome. In addition, these animals provide a means for screening compounds for therapeutic use in GH insensitivity patients (including GH insensitivity which is not associated with a disruption in the GHR), diabetic patients to prevent or reduce end organ damage (e.g., nephropathy) and aging, including premature aging. Further these mice provide a means to examine gene therapy protocols in which alteration of the expression of the GHR in a tissue-specific manner is examined. For example, an expression casette in which the GHR gene is under the transcriptional control of a fat cell-specific promoter (e.g., uncoupling protein I which is expressed specifically in brown fat and uncoupling protein II which is expressed in white fat and other tissues) may be introduced into the fat cells (i.e., adipocytes) of the GHR/BP knockout mice and the effect of fat cell-specific expression of GHR can be examined (i.e., to see if an increase in GHR expression in fat cells decreases the body fat of the mice). The effect of targeted expression of GHR in the tissues that comprise the primary targets of GH action (i.e., muscle, bone, kidney, fat, liver, the eye) may be examined in the GHR/BP knockout mice by placing the GHR gene under the control of a suitable promoter (e.g., the osteocalcin promoter for expression in bone; the albumin promoter for expression in liver; the actin promoter for expression in muscle, etc.).

b. GHR Gene Disrupted Mice

Mice lacking the ability to produce GHR, but which are capable of producing GHBP, are generated using the technique of homologous recombination in ES cells. A targeting vector containing a deletion of the intron located between exon 7 and exon 8A (the intron 7/8A) is used to delete the intron 7/8A. Following homologous recombination into the GHR/BP gene, exon 7 will be directly fused to exon 8A and the neo gene will be inserted into the intron between exon 8A and exon 8. As exon 8A contains a translation stop codon, translation of the GHR mRNA will stop at the end of exon 8A thereby precluding the expression of the GHR.

ES cells containing the homologously recombined targeting vector are injected into blastocysts and chimeric mice derived from the injected blastocysts are mated to produce mice heterozygous for the disrupted GHR/BP gene. Heterozygous mice are then intercrossed to generate homozygous GHR null progeny (homozygous GHR knockouts). The inability to produce functional GHR will produce mice having a dwarf phenotype.

GHR knockout mice may be produced by a variety of means as described above. It is not required that the specific targeting vector described herein be used. Any targeting vector containing a fragment of mouse GHR/BP genomic sequence which is capable of homologously recombining into the mouse GHR/BP gene in a manner that selectively disrupts the GHR/BP gene such that GHR cannot be produce but GHBP cannot be produced may be employed. The targeting vector may be of the replacement- or insertion-type.

The generation of GHR gene disrupted (i.e., knockout) mice need not employ ES cells; targeting vectors or transgenes may be microinjected into mouse oocytes to generate mice containing a disrupted GHR gene. As discussed above, the targeting vector employed need not employ a selectable marker, although the use of a selectable marker is preferred. In addition, chimeric RNA-DNA oligonucleotides containing modified RNA residues (2'-O-methyl modification of the ribose) can be used to target mutations into the GHR/BP gene using ES cells or oocytes to create GHR knockout mice.

Mice containing a disrupted GHR gene find a number of uses. As discussed in more detail below, homozygous GHR knockout mice provide a means for screening compounds beneficial for the treatment of Laron syndrome. In addition, these animals provide a means for screening compounds for therapeutic use in GH insensitivity patients (including GH insensitivity which is not associated with a disruption in the GHR), diabetic patients to prevent or reduce end organ damage (e.g., nephropathy, retinopathy) and aging, including premature aging. Further these mice provide a means to examine gene therapy protocols in which the alteration of the expression of the GHR in a tissue-specific manner is examined as discussed above.

c. GHBP Gene Disrupted Mice

Mice lacking the ability to produce GHBP, but which are capable of producing GHR, are generated using the technique of homologous recombination in ES cells.

Using either a one step or a two step (i.e., a "hit and run" or "tag and exchange" protocol) targeting protocol, the entire intron between exon 7 and exon 8 of the GHR/BP gene is deleted such that exon 7 is directly joined to exon 8. The removal of these gene sequences (intron 7/8) removes exon 8A which encodes the GHBP-specific tail (i.e., carboxy-terminus) which thereby precludes expression of GHBP. However, as exon 8A does not encode sequences found in the GHR, this disruption does not effect expression of GHR.

ES cells containing the homologously recombined targeting vector are injected into blastocysts and chimeric mice derived from the injected blastocysts are mated to produce mice heterozygous for the disrupted GHBP gene. Heterozygous mice are then intercrossed to generate homozygous GHBP null progeny (homozygous GHBP knockouts).

GHBP knockout mice may be produced by a variety of means as described above. Any targeting vector containing a fragment of mouse GHR/BP genomic sequence which is capable of homologously recombining into the mouse GHR/BP gene in a manner that selectively disrupts the GHR/BP gene such that GHBP cannot be produce but GHR can be produced may be employed. The targeting vector may be of the replacement- or insertion-type.

The generation of GHBP gene disrupted (i.e., knockout) mice need not employ ES cells; targeting vectors or transgenes may be microinjected into mouse oocytes to generate mice containing a disrupted GHR gene. As discussed above, the targeting vector employed need not employ a selectable marker, although the use of a selectable marker is preferred. In addition, chimeric RNA-DNA oligonucleotides containing modified RNA residues (2'-O-methyl modification of the ribose) can be used to target mutations into the GHR/BP gene using ES cells or oocytes to create GHBP knockout mice.

IV. Human Disease Associated With Perturbations In GH Expression

In addition to the role GH plays in promoting body growth, this hormone is involved in the regulation of blood glucose levels, the promotion of lactation, aging and may be involved in human tumors (e.g., breast cancer). Administration of GH in adults increases muscle mass and decreases body fat. GH has been shown to have both insulin-like and anti-insulin activities [Salem and Wohff (1989) Proc. Soc. Exp. Biol. Med. 191:113 and Chipkin et al. (1989) Endocrinol. 125:450]; however, it is believed that the primary physiological action of GH is the anti-insulin activity and thus GH action results in hyperglycemia [Davidson (1987) Endocr. Rev. 8:115]. GH, as one of the glucose counterregulatory hormones, has been implicated in diabetes mellitus [Gerich (1986) Scand J. Gastroenterol. 21 (Suppl. 119):154 and Holly et al. (1988) J. Endocrinol. 118:353]. GH levels are elevated in poorly controlled diabetics and elevated GH levels have been implicated in diabetic end organ damage including retinopathy and nephropathy. Transgenic mice which overexpress GH exhibit a giant phenotype and develop glomerulosclerosis that resembles human diabetic nephropathy [Yang et al. (1993) Lab. Invest. 68:62 and Chen et al. (1995) Endocrinol. 136:660]. The development of kidney lesions in transgenic mice overexpressing GH was seen regardless of the presence of absence of diabetes (induced by treatment with streptozotocin) suggesting that GH plays a direct role in diabetic nephropathy [Chen et al. (1996) Endocrinol. 137:5163].

GH and IGF-I have been implicated in ischemia-induced retinal vasoproliferation (neovascularization), the most frequent cause of blindness. GH has been shown to directly stimulate the proliferation of human retinal microvascular endothial cells; IGF-I has a similar effect on retinal endothelial cells. Ischemia-induced retinal neovascularization is the final common pathway in a variety of retinal disorders including diabetic retinopathy, age-related macular degeneration and retinopathy of prematurity. Inhibition of GMl was found to suppress ischemia-induced retinal neovascularization. In addition, GH deficient diabetic patients have a significantly lower incidence of retinopathy than diabetic patients with normal GH secretion [Alzaid et al. (1994) Diabetes Care 17:531]. These findings demonstrate the therapeutic potential of systemic inhibtion oi the GH/IGF-I axis in the treatment of retinopathy.

Variations in GH levels are associated with the aging process in mammals. Ames dwarf mice, which are deficient in GH, prolactin and thyroid-stimulating hormone, have been reported to live significantly longer than their normal siblings and GH deficiency is thought to be particularly relevant to the longer lifespan of these dwarf mice [Brown-Borg et al. (1996) Nature 384:33]. Conversely, overexpression of GH in transgeic mice is associated with a reduced lifespan and other indices of premature aging [Steger et a. (1993) J. Reprod. Fertil. Suppl. 46:61]. Patients with acromegaly and pituitary gigantism have been reported to have reduced lifespans [Pendergrass et aL (1993) J. Cell. Physiol. 156:96].

Given the number of disease states associated with GH and signally through the GHR, animal models which provide a means for identifying compounds which can influence the intracellular targets involved in GH-GHR signalling are needed. Preferred model systems permit the identification of molecular signals which act downstream of the ligand-receptor interaction. The present invention provides such an animal model by providing mice which lack the ability to express functional GHRs. Compounds which are shown to influence growth and other metabolic activities associated with GH action in the transgenic animals of the present invention are thereby identified as influencing intracellular targets in the cascade of signaling associated with the binding of GH to the GHR which are necessarily acting downstream of ligand binding.

IV. Screening Potential Therapeutic Compounds

The present invention provides model systems for the screening of compounds having therapeutic benefit for the treatment of a variety of disease states including Laron syndrome, non-Laron syndrome forms of GH insensitivity (e.g., patients expressing GR which are insensitive to GH) and diabetes. The GHR/BP−/− and GHR−/− mice of the present invention lack the ability to produce functional GHR and therefore, these mice can be used to identify compounds which modulate the second messenger or signalling pathways which act downstream of the binding of the ligand (GH) to its receptor (the GHR); these mice may also be used to identify compounds which modulate the second messenger or signalling pathways which act downstream of the binding of IGF-I to its receptor.

The major aspects of the screening process are discussed in the Experimental section below. Briefly, the chemical compounds being tested will be administered to the transgenic non-human animals of the present invention using any suitable route (e.g., oral, parenteral, rectal, etc.) over a suitable time period (e.g., several months) to determine whether these compounds provide therapeutic benefit for the treatment of a variety of disease states including Laron syndrome, non-Laron syndrome forms of GH insensitivity (e.g., patients expressing GR which are insensitive to GH), GH-induced insulin-resistance and diabetes including diabetic end organ damage such as proliferative diabetic retinopathy and nephropathy.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles);

mmol (millimoles); $\mu$mol (micromoles); nrmol (nanomoles); pmol (picomoles); g (grams); mg (milligrams); $\mu$g (micrograms); ng (nanograms); L (liters); ml (milliliters); $\mu$l (microliters); cm (centimeters); mm (millimeters); $\mu$m (micrometers); nm (nanometers); ° C. (degrees Centigrade); hr (hour); sec (second); min (minutes); kd (kilodaltons); g (unit of force equal to the force exerted by gravity on a body at rest); IV (intravenous); cDNA (complementary deoxyribonucleic acid); mRNA (messenger ribonucleic acid); rRNA (ribosomal ribonucleic acid); PAGE (polyacrylamide gel electrophoresis); Tween (polyoxyethylene-sorbitan); SDS (sodium dodecyl sulfate); EDTA (ethylene diamine tetra-acetic acid); EGTA {[ethylene-bis(oxy-ethylenenitrilo)] tetra-acetic acid};
$MgCl_2$ (magnesium chloride); NaCl (sodium chloride); NaF (sodium fluoride); KCl (potassium chloride); $NaPO_4$ (sodium phosphate); Tris (tris(hydroxymethyl)-aminomethane); HEPES (4-(2-hydroxyethyl)-1-piperazineethanesulfonate); DTT (dithiothreitol); SSC (saline-sodium citrate buffer); NS (not significant); S.E.M (standard error of the mean).

Unless other specified, oligonucleotide primers were obtained from National Biosciences (Plymouth, Minn.), alpha minimal essential medium (Uc-MEM) and fetal calf serum (FCS) were obtained from Gibco (Grand Island, N.Y.) and tested for their ability to support growth of pluripotent ES cells, M2 and M16 medium were obtained from Sigma (St. Louis, Mo.), restriction and DNA modifying enzymes were obtained from New England Biolabs (Beverly, Mass.) and mice were obtained from Jackson Laboratory (Bar Harbor, Me.).

EXAMPLE 1

Construction Of A GHR/BP Targeting Vector

A vector capable of disrupting the mouse GHR/BP gene by homologous recombination was constructed. This replacement type vector contains both a positive and a negative selectable marker which permits the selection of ES cells containing a homologously recombined targeting vector. Homologous recombination of this targeting vector precludes the expression of both GHR and GHBP from the disrupted allele.

a) Isolation Of Genomic Clones Containing Portions Of The Mouse GHR/BP Gene

Figure 1B:
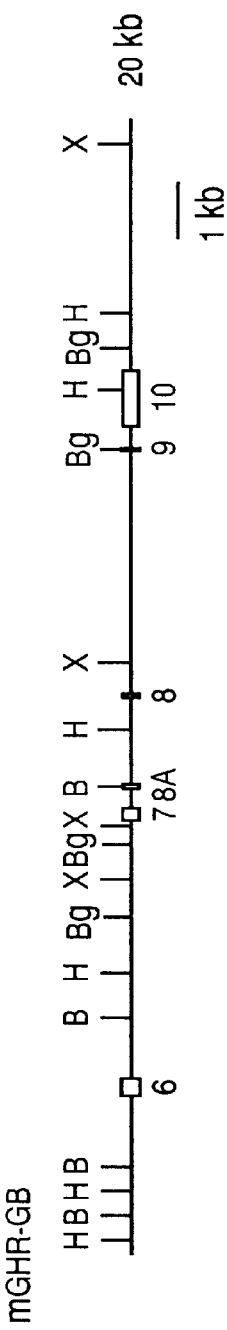
FIG. 1B provides a schematic of the insert contained within the genomic clone mGHR-GB.

A C57 black/6 genomic library constructed using the Lambda Dash II vector (obtained from Stratagene, La Jolla, Calif.) was screened using a full-length mouse GHR cDNA as probe [Zhou et al. (1994) Receptor 4:143]. The sequence of the full-length GHR cDNA is provided in SEQ ID NO:1 and has been assigned GenBank accession no. M33324 Two genomic clones, mGHR-GA and mGHR-GB, were isolated and subsequently subcloned into pUC19 [the nucleotide sequence of a number of genomic mGHR clones can be found under GenBank accession nos.: U49266, U49267, U49268 and U43933]. GHR-GA contained an insert of approximately 16 kb and hybridized to exon 4 of the GHR cDNA. FIG. 1A provides a schematic of the insert contained within mGHR-GA showing the location of several restriction enzyme sites as well as the location of exon 4.

mGHR-GB possessed an insert of approximately 20 kb and hybridized to exons 6–10 of the mGHR cDNA. A schematic showing the location of several restriction enzyme sites as well as the location of exons 6–10 are shown in FIG. 1B. In FIG. 1 the following abbreviations are used: B, BamHI; Bg, BglII; E, EcoRI; H, HindIII; X, XbaI.

Following restriction mapping and nucleotide sequencing of mGHR-GB, a exon which does not have a counterpart in the human GHR gene was revealed and was termed exon 8A [Zhou et al. (1994) receptor 4:223]. Exon 8A encodes the 27 amino acids found at the GHBP carboxy terminus. Also, exon 8A possesses an 81 base 3' untranslated region that contains two tandem and overlapping poly A addition sequences (AAUAA) starting 54 bp downstream from the translational stop codon as well as a rather large AT rich segment in this area. Located between exon 7 and 8A is an intron which possesses the canonical precursor mRNA 5'-splice donor and 3'-splice acceptor sequences. Located between exons 8A and 8 is a 1600 base GHBP 3' flanking region. This sequence encodes the 3' portion of the GHR intron between exons 7 and 8 and contains the 3'-splice acceptor site.

b) Construction Of The pUC19-GA11-neo2-tk Targeting Vector

Figure 2A:
FIG. 2A provides a schematic showing the location of several restriction sites and exon 4 within the mouse genomic DNA insert contained within mGHR-GA.
Figure 2B:
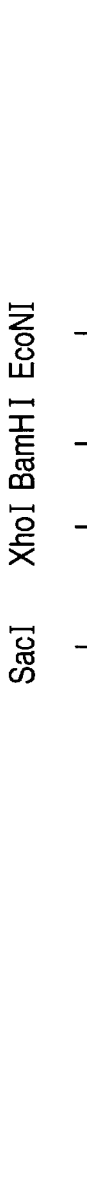
FIG. 2B provides a schematic showing the organization of the GHR/BP targeting vector pUC19-GA11-neo2-tk.
Figure 2C:
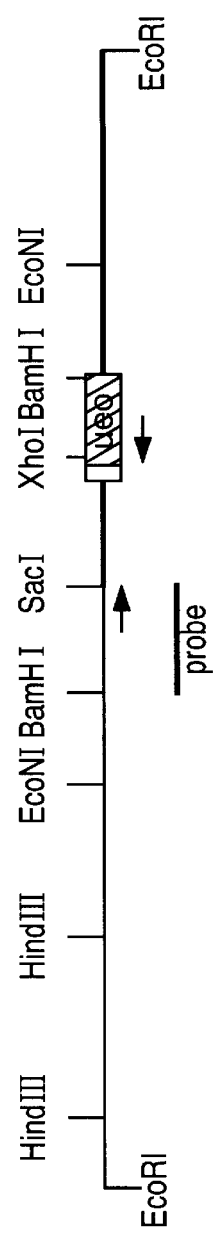
FIG. 2C provides a schematic showing the GHR/BP allele following homologous recombination of the targeting vector into the mouse chromosome.

The pUC19-GA11-neo2-tk targeting vector was derived from GHR-GA as follows. The 6.4 kb SacI-EcoRI fragment containing exon 4 was subcloned into pUC19. FIG. 2A provides a schematic showing the location of several restriction sites and exon 4 within the mouse genomic DNA insert of GHR-GA; the heavy line indicates the 6.4 kb SacI-EcoRI fragment. The resulting plasmid was digested with DraIII followed by treatment with T4 DNA polymerase and all four dNTPs to blunt the overhanging ends. This treatment removed a 500 bp DraIII fragment containing a portion of exon 4. A 1.1 kb neo cassette, in which the neo gene was driven by the HSV promoter flanked by a mutant polyoma enhancer, was obtained by digestion of pSSC9 [Chauhan et al. (1992) Gene 120:281] with XbaI and HindIII followed by treatment with T4 DNA polymerase and dNTPs to blunt the ends [a neo gene driven by the same promoter/enhancer as found in pSSC9 can be obtained from pMC1NeoPoly A (neoR) (Stratagene, La Jolla, Calif.)]. The blunted XbaI-HindIII fragment was then blunt-end ligated to the above-described GHR-GA plasmid such that the 500 bp DraIII fragment was replaced by the neo cassette. Thus, the neo cassette was flanked by GHR/BP gene sequences of 1.1 kb at the 5' end and 4.8 kb at the 3' terminus. A HSV-tk cassette, which served as a negative selection marker, was obtained from pSSC9 by digestion with SfiI and XbaI followed by treatment with T4 DNA polymerase and dNTPs to blunt the ends; the tk gene is driven by the same promoter/enhancer used to express the neo gene. This blunted SfiI-XbaI fragment was placed at the 3' end of the second GHR/BP homologous sequence to generate pUC19-GA11-neo2-tk. FIG. 2B provides a schematic showing the organization of the GHR/BP targeting vector pUC19-GA11-neo2-tk. In FIG. 2B the neo cassette is indicated by the stripped box labelled "neo" and the tk cassette is indicated by the dotted box labelled "tk." Before transfection of ES cells, the targeting vector was linearized by HindIII digestion. FIG. 2C provides a schematic showing the GHR/BP allele following homologous recombination of the targeting vector.

In pUC19-GA11-neo2-tk the DraIII fragment of the GHR/BP genomic sequence was replaced by a functional neo cassette. This replacement deleted the majority of exon 4 as well as the 5' splice donor site and 5' region of intron 4/5. Therefore, the exon 4 of the GHR/BP gene was disrupted. This disruption ablates expression from the GHR/BP gene in the following ways:

1) If a truncated mRNA of GHR/BP which contains exons 1, 2, 3, and 5' region of 4 is generated, the protein would not be functional in terms of GH binding and the subsequent signal transduction process, since it is well known that amino acid residues in exons 4, 5 and 6 are important in GH binding [Godowski et al. (1989) Proc. Natl. Acad. Sci. USA 86:8083; Bass et al. (1991) Proc. Natl. Acad. Sci. USA 88:4498; Amselem et al. (1991) J. Clin. Invest. 87:1098; De Vos et al. (1992) Science 255:306; and Berg et al. (1992) Human Mutat. 1:24]. On the other hand, the deletion of the transmembrane and intracellular domains would also abolish the function of the truncated GHR since the intracellular domain is responsible for transducing GH signals into the cells.

2) The length of an exon can influence RNA splicing [Robberson et al. (1990) Mol. Cell. Biol. 10:84]. Therefore, an artificially large exon with an inserted neo gene may not be recognized by the splicing mechanism and could be skipped. In this case, the skipping of exon 4 would give rise to a mRNA that directly joins exons 3 and 5. However, this will not only generate a deletion of exon 4, but also result in a frame shift mutation starting from exon 5, which will produce a non-functional protein. Similarly, in the event splicing from exons 3 to 6 occurred, the resulting message would lack exons 4 and 5. Splicing from exon 3 to 7 could generate an out-of-frame transcript with deletion of exons 4–6. However, these large deletions should completely abolish GH binding ability of the mutant protein (Godowski et al., supra; Bass et al., supra; Amselem et al., supra; De Vos et al., supra; and Berg et al., supra). Therefore, this targeting vector will essentially ablate the GHR/BP gene.

FIGS. 3A–C-IV provide schematic representations of the targeted disruption of the GHR/BP gene. FIG. 3A depicts the possible pre-mRNA splicing of the disrupted GHR/BP gene. The boxes represent exons and the straight lines represent introns. The neo gene was cloned into exon 4 (25 bp downstream of the start of exon 4) is indicated. I, II, III and IV represent four possible splicing patterns. FIG. 3B1 shows the normal nucleotide (SEQ ID NO:2) and amino acid (SEQ ID NO:3) sequences encoded by the region around the DraIII site in exon 4 which was used for the insertion of the neo gene. FIG. 3B2 shows the nucleotide (SEQ ID NO:4) and amino acid (SEQ ID NO:5) sequences at the junction sites for the spliced wild-type GHR/BP mRNA. FIGS. 3CI-IV show the nucleotide (SEQ ID NOS:6, 8, 10 and 12) and amino acid (SEQ ID NOS:7, 9, 11 and 13) sequences at the splicing sites of the four possible splicing patterns (I–IV) predicted in FIG. 3A. In FIG. 3 "*" indicates translation stop codons. To show disruptions, comparison are made between FIGS. 3B1 and 3C-I, and 3B2 and 3C-II or 3C-III or 3C-IV.

pUC19-GA1-neo2-tk was homologously recombined into the GHR/BP gene in ES cells as described below.

EXAMPLE 2

Generation Of Embryonic Stem Cells Containing A Disrupted GHR/BP Allele

ES cells containing a disrupted GHR/BP allele were generated. This example involved: a) propagation and maintenance of embryonic stem cells, b) electroporation and selection of ES cells and c) screening for GHR/BP targeted ES cell lines and isolation of GHR/BP knockout ES cell clones.

a) Propagation And Maintenance Of Embryonic Stem Cells

The E14 ES cell line [Hooper et al. (1987) Nature 326:292] was cultured either on mitomycin C (Sigma) treated fibroblast cells (from day 12 C57BL/6J mouse fetuses) or in the absence of feeder layer by supplementation with conditioned media containing leukemia inhibitory factor (LIF) [Smith, A. et al. (1988) Nature 336:668 and Williams et al. (1988) Nature 336:684]. LIF-conditioned medium was produced by a LIF expressing COS cell line (Genetics Institute, Cambridge, MA; Smith, A. et al. (1988), supra]. The LIF-expressing COS cell line was grown in alpha minimal essential medium (α-MEM) containing 10% dialyzed fetal calf serum, 10 mg/ml gentamicin and 0.1 mM methotrexate. To produce LIF-containing conditioned medium for supplementing stem cell culture media, the medium of a confluent monolayer of LIF-producing cells was changed to regular stem cell growth medium (see below), incubated for 24 hours and then removed and filtered through a 0.45 μm filter (Millipore). The conditioned medium was then stored up to 3 weeks at 4° C. or frozen at −20° C. for up to one year.

The E14 ES cells were grown in 100 mm cell culture dishes pretreated with a 0.1% porcine gelatin solution (Sigma) for at least 1 hour. The medium used for ES cell culture ("regular stem cell growth medium" or "ES cell medium") was composed of α-MEM supplemented with 20% FCS, 0.1 mM β-mercaptoethanol, 10 mg/ml gentamicin and 1% LIF-conditioned medium. The cells were cultured at 37° C. in an atmosphere of 5% $CO_2$ and 95% air at a pH of 7.2–7.4. Culture medium was changed every two days to keep cultures in an optimal condition. Cells were passed (1:5 to 1:7 dilution) or frozen upon confluence when necessary [Joyner (1993) *Gene Targeting: A Practical Approach*, Rickwood (ed.), Oxford University Press, NY and Hogan et al. (1994) *Manipulating the Mouse Embryo: A Laboratory Manual*, 2nd Ed., Cold Spring Harbor Laboratory Press, NY].

ES cells were frozen in ES cell culture medium containing 10% DMSO as a cryoprotector ("freezing medium"). As a general rule, cells were frozen slowly and thawed quickly. For long-term freezing of the ES cell stocks (Joyner, supra and Hogan et al, supra), cells in a 100 mm dish were trypsinized with 0.05% trypsin/EDTA, pelleted by centrifugation (270×g, 5 min) and resuspended in 1.5 ml ES cell medium. One and one half ml of ES medium containing 20% DMSO was added into the cell suspension on ice. The well-mixed cell suspension was aliquoted into 1 ml freezing vials on ice and transferred to a –70° C. freezer in a pre-cooled Styrofoam® box. Twenty-four hours later, cells were transferred to liquid nitrogen.

Identification of homologous recombinants can require screening large numbers of ES cell colonies. Large numbers of ES cell lines were frozen on feeders in 24-well tissue culture plates for a short term during the identification process (Joyner, supra and Hogan et al., supra). This was done by removing the medium, adding 0.25 ml of 1× cold freezing medium per well on ice, and transferring the plates to a pre-cooled Styrofoam® box in a –70° C. freezer.

b) Electroporation And Selection Of ES Cells

ES cell transfection and selection were performed as previously described with minor modifications (Joyner, supra and Hogan et al., supra). Briefly, 1×10⁷ E14 ES cells were suspended in 0.8 ml of ice-cold PBS containing 30–40 μg of GHR/BP targeting vector linearized with HindIII. The cell suspension was placed on ice for 10 min and then electroporation was carried out using a Gene-Pulser (Bio-Rad) at 240 V and 500 μF. Cells were then placed on ice for 10 min before splitting into three 100 mm tissue culture dishes containing LIF-conditioned ES cell medium. Twenty-four hours after electroporation, G418 (300 μg/ml) and gancyclovir (2 μM) were added into the culture medium ("selective medium") to select for neo and against tk gene expression [the surviving cells are said to be resistant to G418 ($G418^r$) and gancyclovir ($GAN^r$)]. Culture medium was changed every day during the entire selection process.

Ten days after electroporation with linearized targeting vector and selection with G418 and gancyclovir, individual colonies (ES clones) were isolated and expanded in LIF-conditioned ES medium (without G418 and gancyclovir) in 24 well tissue culture plates containing feeder layers. Upon near confluence, cells were passed into two 24-well plates, one with feeder layer for freezing (see above) and later studies, and the other without feeder layers for DNA analysis. These colonies were analyzed for homologous recombination events by Southern blotting and PCR analyses. As shown in Table 1, three separate transfections were performed using the E14 ES cell line.

TABLE 1

| Experiment | No. Of Cells Transfected | $G418^r$, $GAN^r$ Clones | Knockout Clones (%) |
|---|---|---|---|
| 1 | 1 × 10⁷ | 234 | 1 (0.43) |
| 2 | 1 × 10⁷ | 144 | 2 (1.39) |
| 3 | 1 × 10⁷ | 144 | 0 (0) |

A total of 522 $G418^r$, $GAN^r$ E14 ES cell clones were isolated and screened by Southern blot analysis (described below). When genomic DNA isolated from the $G418^r$, $GAN^r$ E14 ES cell clones was digested with BamHI and probed with the A12 probe, in addition to the endogenous 15 kb band, an additional band of ~4 kb was detected in three clones. These three clones were termed E14-D3, E14-D5 and E14-D6. As described below the E14-D3 and E14-D5 clones, but not the E14-D6 clone, were shown to contain a homologously recombined targeting vector. Thus, the overall gene targeting frequency was approximately $10^{-7}$.

c) Screening For GHR/BP Targeted ES Cell Lines And Isolation Of GHR/BP Knockout ES Cell Clones When $G418^r$, $GAN^r$ ES clones grown in 24 well plates without feeder layers reached confluence, genomic DNA was isolated as described [Ramirez-Solis et al. (1992) *Analytical Biochem.* 201:331]. Southern blot and PCR analysis were employed to screen for GHBP or GHR knockout ES cells. Briefly, genomic DNA isolated from the ES clones was digested with BamHI. An aliquot comprising approximately one-tenth of the digested DNA for each sample was taken for PCR analysis. Nine-tenths of the ES cell genomic DNA was loaded on a 0.8% agarose gel and resolved at 40 V for 2–3 hours. The DNA was then transferred to nitrocellulose membranes and hybridized with $^{32}$P-labeled probe, A12. The A12 probe is a 1.6 kb BamHI-SacRI fragment located upstream of exon 4; the location of this probe fragment within a chromosome containing a homologously recombined targeting vector is shown schematically in FIG. 2C (the solid bar labelled "probe").

Since a BamHI site was introduced into the targeting vector with the insertion of the neo cassette (FIG. 2B), BamHI digestion was used in Southern blot analysis to screen for ES cell lines which have undergone a homologous recombination event (FIG. 2C). DNA corresponding to the A12 probe is not present in the targeting vector (FIG. 2). Upon Southern blot analysis (BamHI digestion), $G418^r$, $GAN^r$ ES cells containing one disrupted GHR/BP allele (single-allele knockout cells) produce a band of approximately 4 kb as well as a 15 kb endogenous band in the GHR/BP. $G418^r$, $GAN^r$ ES cells containing a randomly inserted targeting vector produce only the 15 kb band. If both alleles are disrupted, only a single 4 kb band would be seen upon Southern blot analysis using the A12 probe.

Figure 4:
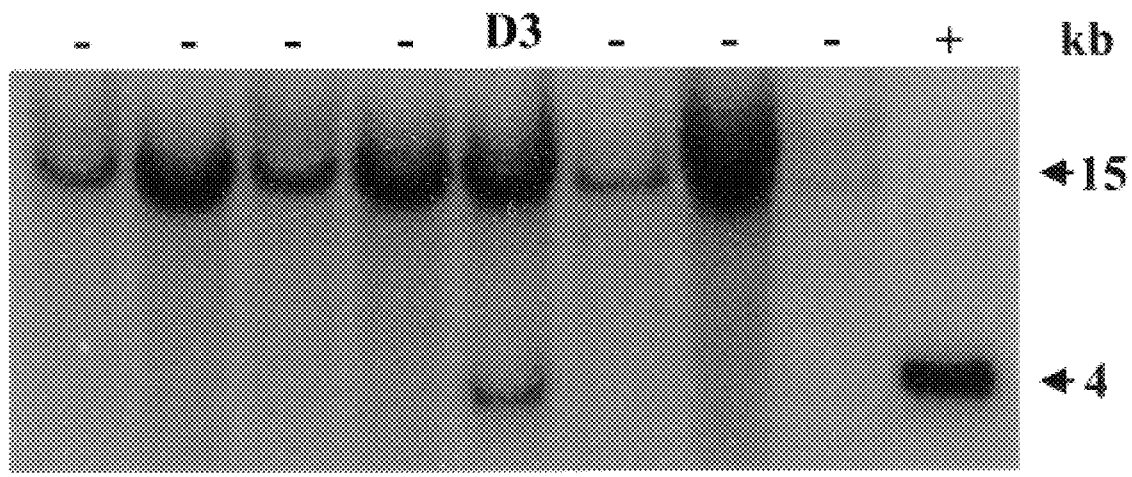
FIG. 4 shows a Southern blot generated using genomic DNA isolated from G418$^r$, GAN$^r$ ES cells which were transfected with the GHR/BP targeting vector, digested with BamHI and hybridized with probe A-12.

FIG. 4 shows a representative Southern blot using genomic DNA isolated from $G418^r$, $GAN^r$ ES cells, digested with BamHI and hybridized with probe A-12. pUC19-GA11-neo2-tk was used as a positive control (lane 9 marked "+"). In FIG. 4 "–" indicates that the cell line examined is negative for homologous recombination of the targeting vector (i.e., only the 15 kb endogenous band was observed). ES cell clone D3 (lane 5) was considered to be a GHR/BP knockout ES cell line because it demonstrated a 4 kb recombinant band and a 15 kb endogenous band.

If the expected band indicating homologous recombination was observed by Southern blot analysis, PCR was done to verify that these ES cell clones had undergo a homologous recombination event. PCR primers were the upstream A12-2 primer: 5'-CCAAGCTCCTACAGAACATCCCA-3' (SEQ ID NO:14) and the downstream neo-3 primer: 5'-GCTCGACATTGGGTGGAAACAT-3' (SEQ ID NO:15). The PCR conditions comprised 40 cycles of 94° C. for 30 sec, 58° C. for 30 sec, and 72° C. for 90 sec. The A12-2 primer hybridizes to sequences located in the 1.6 kb BamHI/SacI fragment and the neo-3 primer hybridizes to sequences located in the neo gene cassette. G418$^r$, GAN$^r$ ES cells which contain a homologously recombined targeting vector permit the amplification of a 1.2 kb fragment; this fragment cannot be amplified in cells lacking a homologously recombined targeting vector. A representative PCR analysis is shown in FIG. 5.

Figure 5:
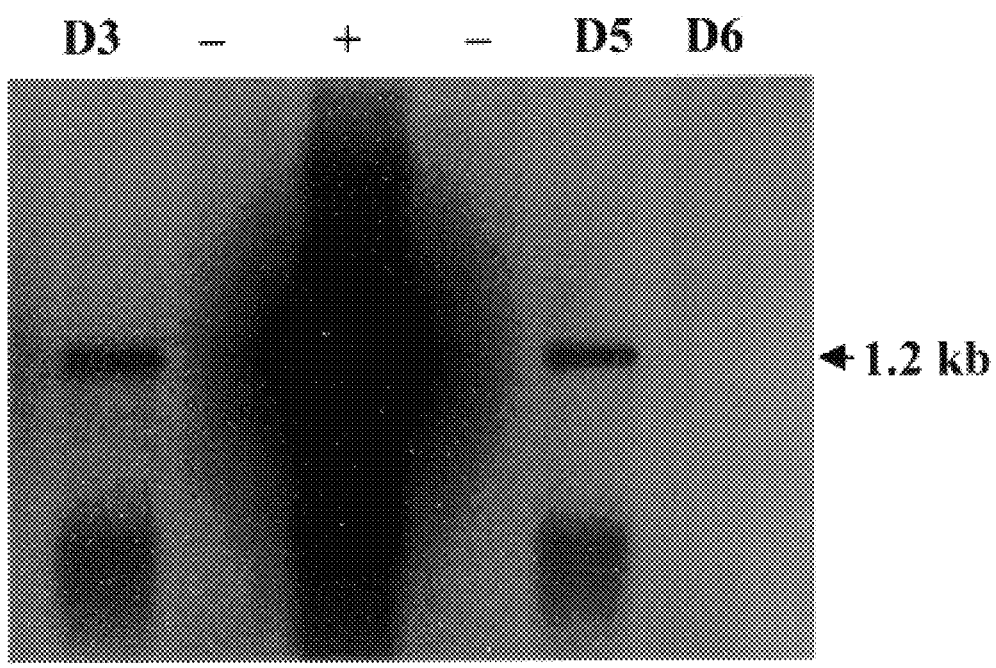
FIG. 5 depicts the PCR analysis of genomic DNA isolated from ES cells transfected with the GHR/BP targeting vector.

For the data shown in FIG. 5, 500 ng of genomic DNA isolated from G418$^r$, GAN$^r$ ES cell clones D3, D5 and D6 as well as from two G418$^r$, GAN$^r$ ES cell lines ("−") which did not undergo homologous recombination or 500 pg of pUC19-GA11-neo2-tk plasmid DNA were employed as templates in the PCRs which contained the A12-2 and neo-3 primers. The PCR products were radiolabeled using $^{32}$P-dATP during the amplification reactions. PCR products were resolved on a 1% agarose gel, the gel was dried and exposed to X-ray film. As shown in FIG. 5, a 1.2 kb product was amplified using DNA isolated from ES cell clones D3 and D5 as well as the positive control plasmid (pUC19-GA11-neo2-tk) but not from either D6 cells or the negative control cells.

ES cell lines which displayed a 4 kb band upon probing of Southern blots with the A12 probe were expanded from the frozen plates and half of the expanded cells were frozen at each passage to keep cells in good germ line competence. To further confirm the presence of a homologously recombined targeting vector in these cell lines, Southern blot analyses were performed using BamHI, EcoNI and HindIII plus XhoI digestion of genomic DNA isolated after 10–14 passages. These blots were probed with the DNA fragment, A12 (FIG. 2C). PCRs, conducted as described above, were also performed on the expanded cultures.

Figure 6:
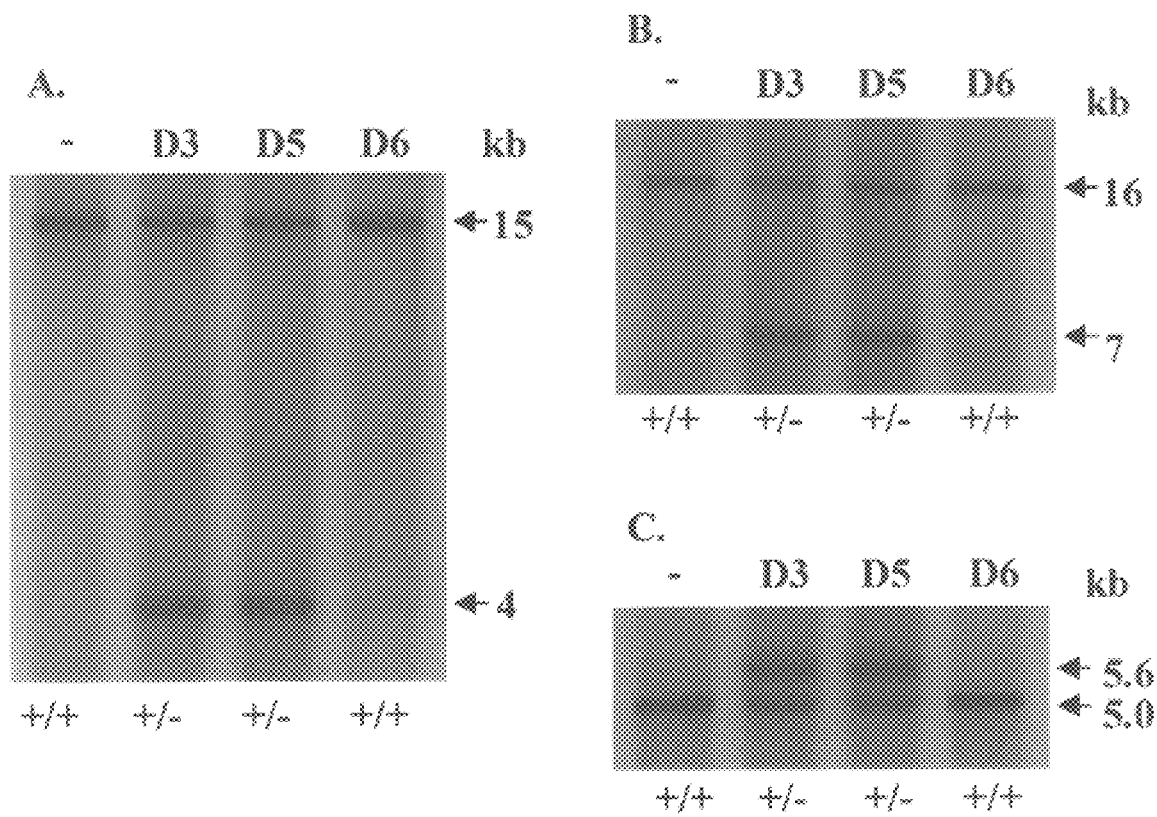
FIGS. 6A–C show autoradiograms of Southern blots generated using genomic DNA isolated from GHR/BP knockout and control ES cells.

FIGS. 6A–C show autoradiograms of Southern blots from the expanded knockout cell lines. For the data shown in FIG. 6, approximately 20 μg of genomic DNA isolated from GHR/BP knockout (lines D3, D5 and D6) and control (−) E14 ES cells were digested with BamHI (FIG. 6A), XhoI and HindIII (FIG. 6B) and EcoNI (FIG. 6C). In FIG. 6, "+" indicates the presence of a wild-type or undisrupted GHR/BP allele and "−" indicates the presence of a disrupted GHR/BP allele. When A12 was used as the probe, BamHI digestion produced two bands (15 and 4 kb) in E14-D3 and E14-D5 cells. EcoNI generated a 5 kb band and a 5.6 kb band because the neo cassette replacing the DraIII fragment of pUCI 9-GA 11 is about 500 bp whereas the neo gene is 1.1 kb. Thus, this replacement increased the size of the EcoNI fragment from 5 kb to 5.6 kb. Since the introduction of the neo cassette into the targeting vector also introduced an XhoI site (FIG. 2), this change decreased the size of the 16 kb HindIII/XhoI fragment of the mHR/BP gene to 7 kb (FIG. 2). The results shown in FIG. 6 confirmed that E14-D3 and E14-D5 contain a disrupted GHR/BP gene in one allele. However, the result for E14-D6 is not consistent with what was observed in the screening process. The reason for this inconsistency has not been determined and is not necessary for an understanding of or the use of the present invention.

The Southern blot results obtained using the expanded clones were also confirmed by PCR analysis using the A12-2 and neo-3 primers; a 1.2 kb product was amplified from E14-D3 and E14-D5 cells, but not from E14-D6 nor form another other cells.

Thus, 2 ES cell lines, E14-D3 and E14-D5, containing a disrupted GHR/BP gene, were established.

EXAMPLE 3

Production Of Chimeric GHR/BP Gene Disrupted Mice

ES cells containing a disrupted GHR/BP gene were used to generate chimeric mice. This experiment involved: a) preparation of mice for embryo recovery and transfer, b) embryo recovery, microinjection and transfer, c) production of chimeric GHR/BP gene disrupted mice and d) production of heterozygous GHR/BP gene disrupted mice.

a) Preparation Of Mice For Embryo Recovery And Transfer

Mice were prepared according to the methods described by Joyner (supra). Briefly, female Balb/c mice to be used for embryo recovery were paired with stud Balb/c males in the late afternoon of the fourth day before blastocyst recovery. The female mice were checked for vaginal plugs in the morning of the third day before embryo recovery. These plugged mice were used for embryo collection.

For preparation of foster mothers, female Balb/c mice were paired with vasectomized Balb/c males in the late afternoon of the third day before embryo transfer. Vaginal plugs were checked the next day after pairing. These plugged mice were then used as foster mothers.

b) Embryo Recovery, Microinjection And Transfer

Embryo recovery and transfer were performed as described by Joyner (supra). Briefly, the pregnant animals were sacrificed on the fourth day of pregnancy by cervical dislocation. The uteri were removed and flushed with approximately 0.5 ml of M16 medium through each horn of the uterus. Embryos settled to the bottom of the flush dish and were transferred to a watchglass or the micromanipulation chamber or dish containing fresh M16 until microinjection. Twelve to fifteen ES cells from a single cell suspension were injected into the blastocoel cavity of each blastocyst. Approximately 10 blastocysts were transferred into the uterus of each pseudopregnant female mouse.

c) Production Of Chimeric GHR/BP Gene Disrupted Mice

A total of 140 Balb/c blastocysts were injected with GHR/BP knockout E14 ES cells (Table 2). Approximately 10 to 15 GHR/BP knockout ES cells (D3, D5 and D6) were injected per blastocyst. Ten to 12 injected blastocysts were transferred into the uterus of foster mother mice at day 2.5 of pseudopregnancy.

i) Identification Of Chimeric Mice

The most convenient and readily apparent genetic marker of chimerism is coat color. Balb/c mice are albino while 129/Ola mice have a chinchilla colored coat. The E14 ES cells were derived from 129/Ola mice. Therefore, the chimera display a white background with chinchilla spots or stripes on the coat, which indicates that the cells were derived from the injected ES cells. The chimeric contribution of the ES cells in a chimera is likely proportional to the their contribution to coat color. This is also correlated to germline transmission (Joyner, supra).

TABLE 2

| Cell Line | # Of Blastocysts Transferred | # Of Mice Born Alive ♀ | # Of Mice Born Alive ♂ | # Of Chimeric Mice ♀ | # Of Chimeric Mice ♂ |
|---|---|---|---|---|---|
| D3 | 20 | 2 | 1 | 0 | 0 |
| D5 | 98 | 5 | 6 | 3 | 3 |
| D6 | 22 | 3 | 2 | 1 | 1 |
| Total | 140 | 10 | 9 | 5 | 3 |

As shown in Table 2, eleven offspring were born from embryos injected with E14-D5 ES cells, of which 3 male and 3 female mice were chimeric. Chimerism was determined by coat color. Three pups were derived from blastocysts injected with E14-D3 ES cells. However, none of them were chimeric. Since the E14 ES cells were isolated from a male embryo, female chimeras rarely transmit via the germline [Kuehn et al. (1987) Nature 326:295]. Only the male chimeras were bred to produce heterozygous GHR/BP knockout mice.

Chimeric mice had approximately 30 to 60% of their coat originating from the injected ES cells. According to the literature (Joyner, supra), these mice have a relatively high possibility of transmitting their manipulated germline to offspring. Therefore, they were bred with normal Balb/c females to generate heterozygous and ultimately homozygous GHR/BP knockout mice.

d) Production Of Heterozygous GHR/BP Gene Disrupted Mice

Animals derived from blastocysts injected with GHR/BP knockout ES cells were separated on the 30th day after birth. At about 45 days after birth, male chimeric mice ere bred with normal female Balb/c mice of the same age for the production of heterozygous GHR/BP gene disrupted mice. The female Balb/c mice were checked for vaginal plugs every day and the plugged mice were placed in a separate cage. The rate of germline transmission to offspring was determined on the basis of coat color (i.e., chinchilla coat color). Offspring were separated at day 30 after birth. Genomic DNA was isolated from the tails of heterozygous mice (i.e., chinchilla mice) and analyzed for the presence of the homologously integrated targeting vector by Southern blot analysis using BamHI digestion and hybridization with either the A12 fragment or neo gene as probe. Heterozygous GHR/BP gene disrupted mice were inbred to produce homozygous knockout mice. Homozygosity was confirmed by Southern blot analysis.

The result for production of heterozygous GHR/BP gene disrupted mice is summarized in Table 3.

TABLE 3

Production Of GHR/BP Knockout Mice

| Chimeric Founder | # Of Litters | Total # Of Pups | # Of Chinchilla Pups | # Of Knockout Mice |
|---|---|---|---|---|
| # 6 | 13 | 123 | 0 | 0 |
| # 8 | 7 | 64 | 64 | 24 |
| # 11 | 15 | 127 | 3 | 1 |

As shown in Table 3, out of the three chimeric mice, mouse #8 transmitted the GHR/BP gene disruption through the germline to all of his 64 offspring, such that all 64 mice were chinchilla in coat color. Chimera #11 transmitted the gene disruption through the germline to 3 of his 127 pups. Since only one allele was disrupted in the ES cells, it was expected that about 50% of these mice would be heterozygous knockout animals. When genomic DNA from the 64 pups sired by founder #11 was analyzed by Southern analysis, 24 showed a 15 kb endogenous band and a 4 kb band derived from the targeting vector when the genomic DNA was digested with BamHI and hybridized to the A12 fragment probe; only the 15 kb endogenous band was detected in all other mice (FIGS. 7A–B).

The results shown in FIGS. 7A-B depict Southern blot analysis of genomic DNA isolated from heterozygous mice. Genomic DNA was isolated from 31 heterozygous mice (chinchilla) sired by founder #11 and digested with BamHI. The digested DNA was resolved on a 0.8% agarose gel, transferred to a nitrocellulose membrane and hybridized to the A12 and neo probes (as indicated). In FIG. 7, "C" indicates the positive control, pUC19-GA11-neo2-tk; "+/+" indicates animals homozygous for the wild-type GHR/BP allele; and "+/−" indicates mice heterozygous for the GHR/BP disrupted allele.

The results shown in FIGS. 7A–B result suggests that the nine animals showing the 4 kb band upon Southern analysis using the Al12 probe are heterozygous knockout mice carrying a disrupted GHR/GHBP gene in one allele that has been derived form the injected ES cells. When the genomic DNA blots were hybridized to a neo gene probe, only a single 4 kb band was detected in the 24 knockout mice but not in the others (FIG. 7). This result demonstrated that the targeting vector specifically replaced the endogenous homologous sequence without random integration.

EXAMPLE 4

GHR/BP Knockout Mice Provide An Animal Model For Human Laron Syndrome

Mice containing one or two GHR/BP disrupted alleles were generated and characterized. As shown below, homozygous GHR/BP mice provide an animal model for Laron syndrome.

a) Production Of Homozygous GHR/BP−/− Mice

Heterozygous GHR/BP+/− knockout mice were mated to produce homozygous GHR/BP−/− mice. Disruption of the mGHR/BP gene was confirmed by Southern blot Southern blot analysis of genomic DNA using BamHI digestion and the blots were hybridized with the A12 or neo gene probes. In addition, RT-PCR, Western blotting (described below) and serum GHBP analyses (described below) were conducted to confirm disruption of the mGHR/BP gene.

Genotyping of 243 offspring from GHR/BP+/− breeding revealed a frequency of 26% GHR/BP+/+, 51% GHR/BP+/− and 23% GHR/BP−/− mice, consistent with Mendelian genetics. The average litter size from GHR/BP+/− breeding was 6.57 pups (range: 3–13 pups/litter), within the same litter size of GHR/BP+/+ at the same breeding age. The sex distribution of GHRIBP+/− offspring was normal for all three genotypes of offspring. Inbreeding of GHR/BP−/− mice gave an average of 2.71 pups/litter, which is significantly smaller than those derived from GHR/BP+/+or GHR/BP+/− breeding. The average age of first pregnancy for GHWBP+/+ females was approximately 10 weeks, compared to 6 weeks for GHR/BP+/+ and GHRIBP+/− mice. In addition, the mortality of newborn GHR/BP−/− offspring (26.3%) was significantly higher than that seen in GHR/BP+/+ offspring (5%) and GHRvBP+/− offspring (6%). Out of 6 dead newborn of GHR/BP+/− breeding, 2 were G3HRIBP+/+, 3 were GHR/BP+/− and 1 was GHR/BP−/−. Neither abnormal embryonic lethality nor unusual newborn deaths were observed for GHR/BP−/− offspring from GHR/BP+/− inbreeding. Therefore, the smaller litter size and higher mortality observed in GHR/BP−/− mice may be derived from the mothers or the fathers in the case of delayed pregnancy and smaller litter size. Delayed sexual development for both male and female Laron syndrome patients has been reported [Rosenbloom et al. (1992) Acta Pediatr. (Suppl.) 383):121 and Pelizelan et al. (1993) Pediatr. Adolescent. Endocrinol. 24:27].

b) Homozygous GHR/BP Knockout Mice Are Approximately 40–50% Smaller Than Normal Littermates The body growth rate of normal mice and heterozygous and homozygous GHR/BP knockout mice was determined as follows. Body weight was determined every ten days starting at day 30 after birth. The body weight of heterozygous knockout mice was compared to normal (i.e., non-transgenic) litter mates using a Student t test.

Figure 8A:
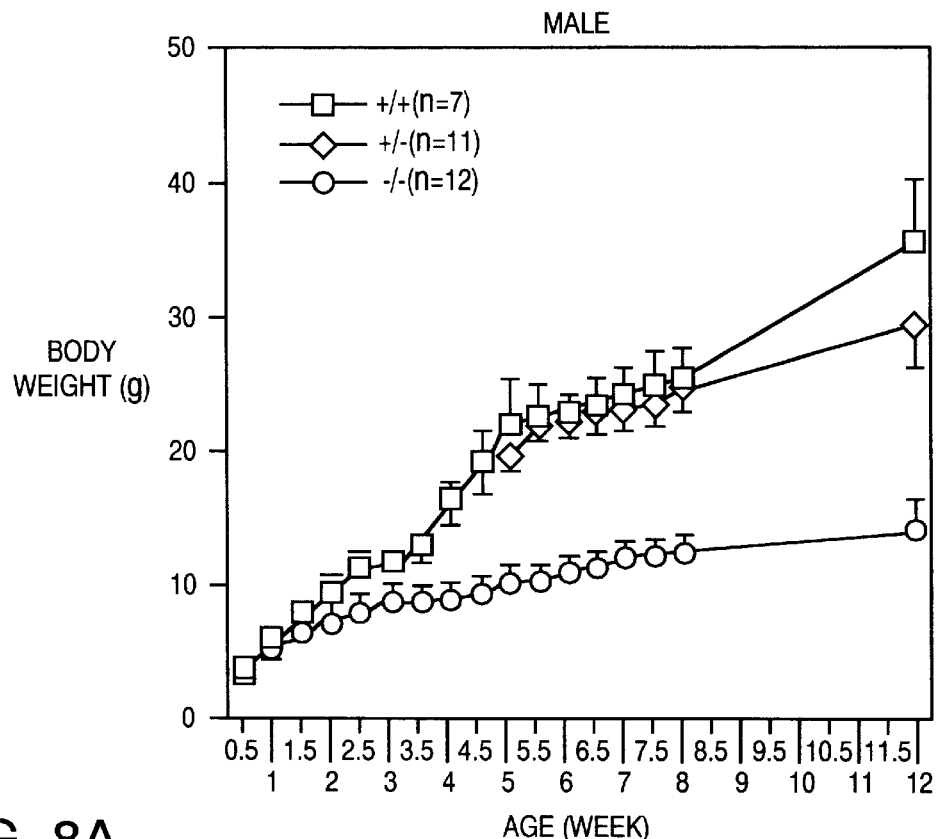
FIGS. 8A and 8B show the body weight of male (8A) and female (8B) GHR/BP+/+, GHR/BP+/− and GHRIBP−/− mice plotted against age.
Figure 8B:
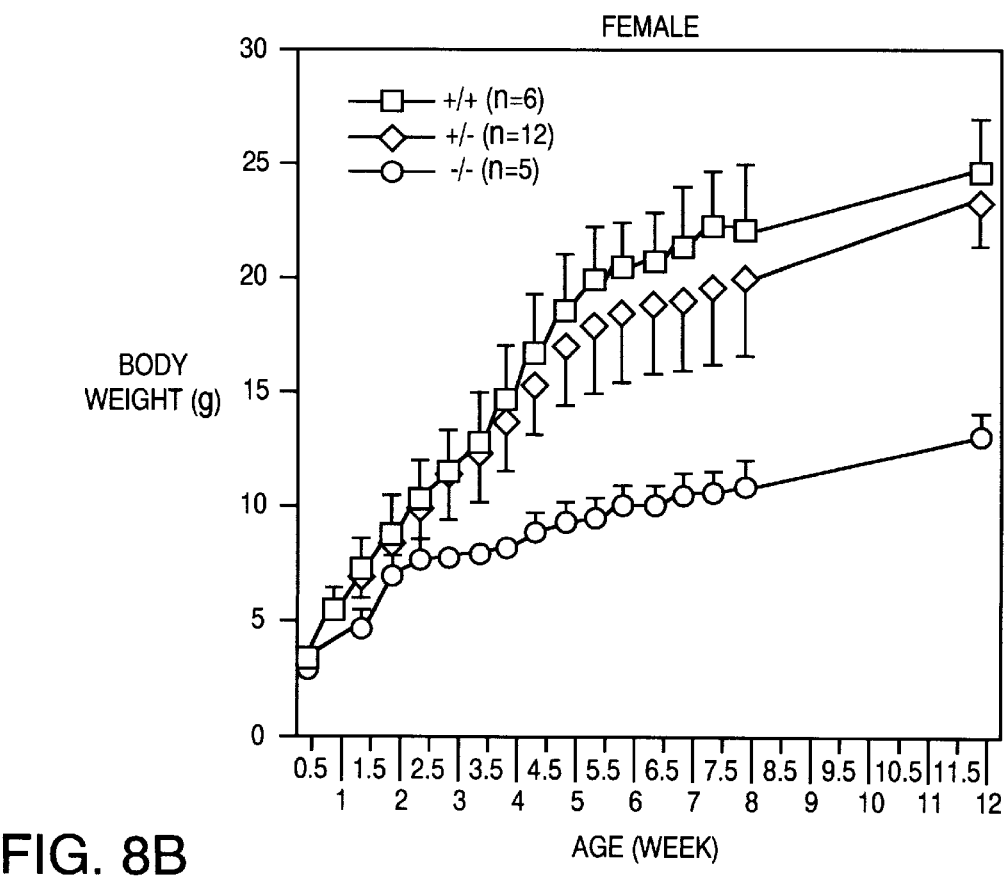

No significant body size or w eight differences at birth was observed among GHRiBP+/+, GHR/BP+/− and GHR/BP−/− littermates. At week 3 after birth, the GHR/BP−/− mice appeared significantly smaller than both GHR/BP+/+ and GHR/BP+/− mice while GHR/BP+/− mice were not significantly smaller than GHR/BP+/+ littermates. With age, the difference in body size or weight increased progressively (FIGS. 8A and 8B). In FIGS. 8A and 8B, the body weight in grams (g) is plotted against age (in weeks) for male (8A) and female (8B) mice. In FIGS. 8A–B, the open squares, filled diamonds and open circles represent GHR/BP+/+, GHR/BP+/− and GHRIBP−/− mice, respectively.

Figure 8C:
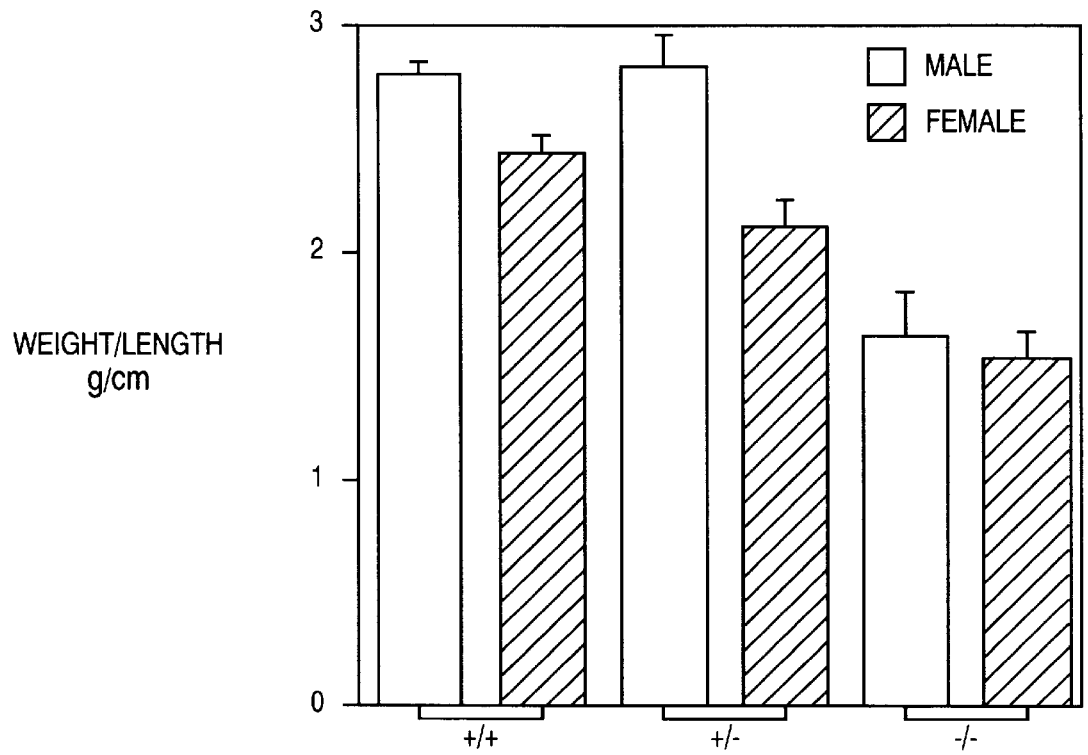
FIG. 8C depicts the weight/length ratio of 8 week GHR/BP+/+, GHR/BP+/− and GHR/BP−/− mice.
Figure 8D:
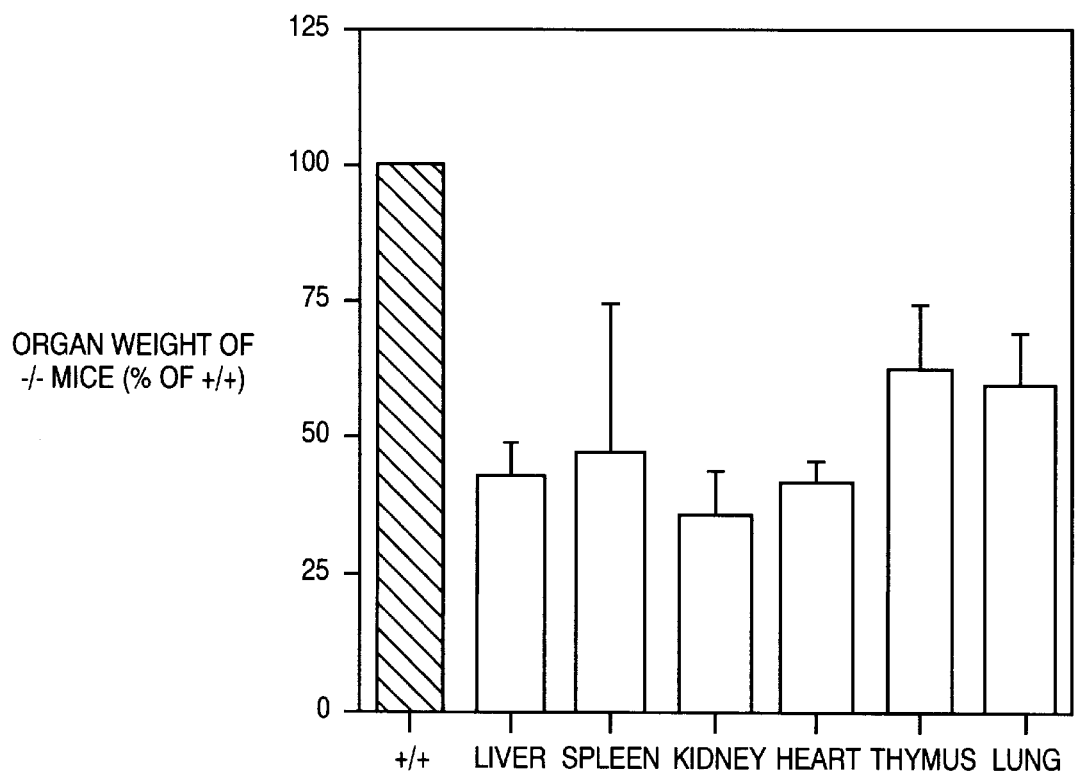
FIG. 8D shows the weight of major organs taken from GHR/BP−/− mice in comparison to organs from GHR/BP+/+ mice.

As shown in FIGS. 8A–B, at 12 weeks after birth the mean body weight of GHR/BP+/− mice appeared smaller than that of GHR/BP+/+ mice. However, this difference was not statistically significant. The behavior of GHR/BP+/− and GHR/BP−/− mice was indistinguishable from that of GHR/BP+/+mice. The body weight/length ratio of 8 week old GHR/BP−/− mice was significantly decreased when compared to GHR/BP+/− and GHR/BP+/+ littermates (FIG. 8C; shaded and filled columns represent male and female mice, respectively). Such differences between GHR/BP+/− and GHR/BP+/+ mice was not obvious. While not limiting the present invention to any particular mechanism, this may be caused by a change in the body composition of GHR/BP−/−. The weights of major organs of GHR/BP−/− mice were also decreased compared to GHR/BP+/+ littermates (FIG. 8D), with liver, kidney and heart being effected the most (these organs were less than 50% the weight of those in GHR/BP+/+ mice); in FIG. 8D, the weight of the indicated organs from GHR/BP−/− mice is plotted as a percentage of the weight of the corresponding organ in GHR/BP+/+ mice. These findings are consistent with the fact that GHR and GHBP mRNAs are most abundant in these tissues [Herington et al. (1991) Acta Endocrinol. 124:14], implying that growth of these organs are more dependent on GH.

c) GHR Protein Is Undetectable In Homozygous GHR/BP−/− Mice

GHR expression in GHR/BP+/+, GHR/BP+/− and GHR/BP−/− mice by Western blotting analysis. Protein extracts (whole cell lysates prepared by placing cells in boiling lysis buffer containing 1% SDS, 10 mM Tris-HCI, pH 7.4) were prepared from livers isolated from GHR/BP+/+, GHRJBP+/− and GHR/BP−/− mice and separated by electrophoresis on a 4–12% gradient SDS-PAGE gel. The separated proteins were transferred to nitrocellulose and the blot was probed using GHR antisera (polyclonal GHR antiserum provided by Drs. G. P. Frick and M. Goodman, Univ. of Mass. Medical School, Worcester, Mass.). The resulting blot is shown in FIG. 9A.

Figure 9A:
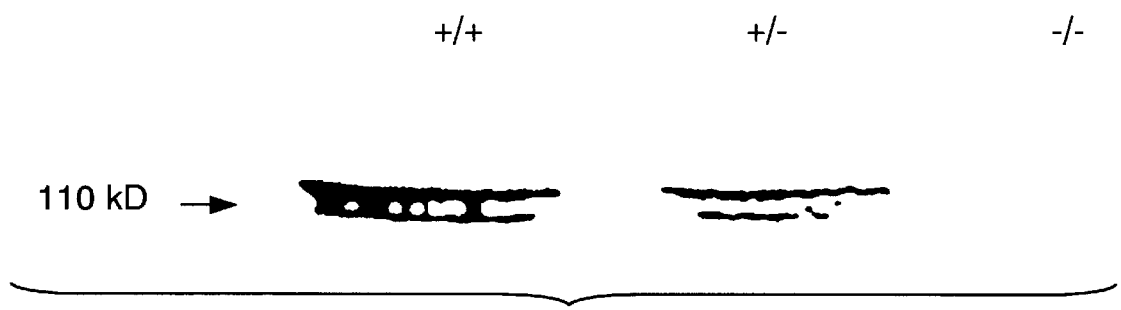
FIG. 9A shows a Western blot which indicates the level of GHR protein present in the liver of GHR/BP+/+, GHR/BP+/− and GHR/BP−/− mice.

In FIG. 9A, the apparent molecular weight of the mGHR is indicated (110 kD). Proteins from GHR/BP+/+, GHR/BP+/− and GHR/BP−/− mice are shown from left to right, respectively in the blot.

As shown by the results shown in FIG. 9A, no detectable GHR protein was observed in GHR/BP−/− mice and the level of GHR protein in GHR/BP+/− mice was about ½ the level observed in GHR/BP+/+ mice.

d) Serum GHBP Levels Are Undetectable in Homozygous GHR/BP−/− Mice

Figure 9B:
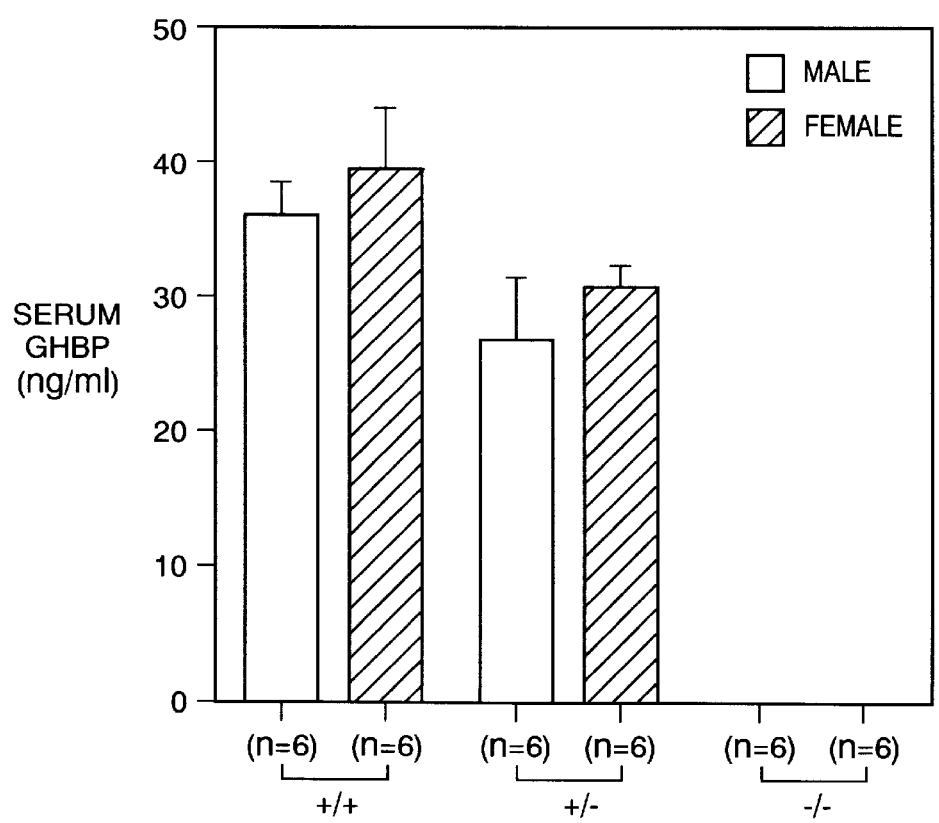
FIG. 9B is a graph showing serum GHR/BP levels in male and female GHR/BP+/+, GHR/BP+/− and GHR/BP−/− mice.

Serum GHBP levels were measured in GHR/BP+/+, GHR/BP+/− and GHR/BP−/− mice. Sera was collected from 6 male and 6 female mice of each genotype and GHBP levels were determined as described [Baumannr et al. (1987) J. Clin. Endocrinol. Metab. 65:814 and Daughaday and Trivedi (1987) Proc. Natl. Acad. Sci. USA 84:4636]. Briefly, sera (0.4 ml) was incubated with $10^5$ cpm (~1 ng) monomeric $^{125}$I-hGH with or without varying concentrations of unlabeled hGH (0–4 mg/ml) in PBS/0.1% BSA in a final volume of 0.5 ml for 45 min at 37° C. Bound GH was then separated from free GH by gel filration and determined by gamma counting. The GHBP concentration was calculated from the binding data, taking dissociation during chromatography into account The results are summarized in FIG. 9B. In FIG. 9B, serum GHBP levels (ng/ml) are shown for male (shaded columns) and female (filled columns) normal (+/+), heterozygous (+/−) and homozygous (−/−) GHR/BP disrupted mice.

As shown in FIG. 9B, no detectable serum GHBP was seen in GHR/BP−/− mice. The lack of detectable serum GHBP in GHR/BP−/− mice is consistent with the findings in a majority of Laron syndrome patients.

d) IGF-1 Levels Are Greatly Reduced In Homozygous GHR/BP Mice

Figure 10:
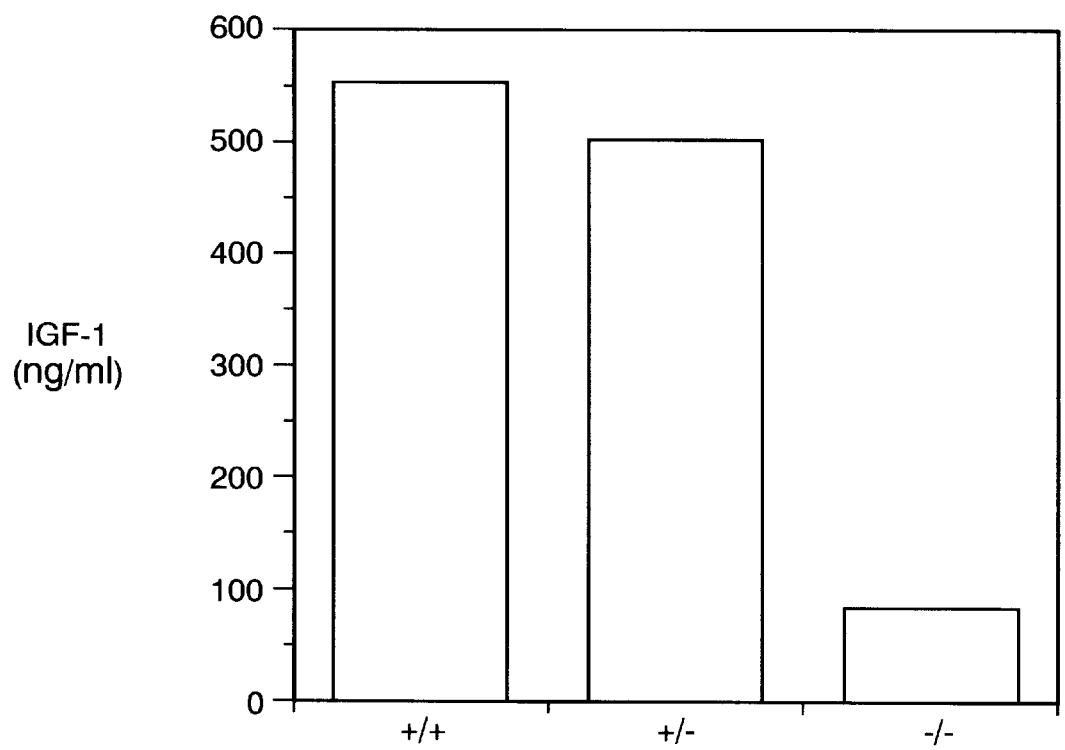
FIG. 10 is a graph showing serum IGF-I levels in GHR/BP+/+, GHR/BP+/− and GHR/BP−/− mice.

Serum IGF-I levels were measured using acid-ethanol serum extracts by use of an IGF-I radioimmunoassay kit according to the manufacturer's instructions (Nichols Institute, San Juan Capistrano, Calif.) as described [Daughaday et al. (1980) J. Clin. Endocrinol. Metab. 51:781 and Chen et al. (1991) Endocrinol. 128:1402]. FIG. 10 summarizes IGF-I levels (ng/ml) measured in wild-type mice (+/+), heterozygous GHR-BP knockout mice (+/−) and homozygous GHR(BP knockout mice (−/−).

The results shown in FIG. 10 demonstrate that the serum IGF-I levels of GHR/BP−/− mice were ten-fold lower than that observed in GHR/BP+/+ and GHR/BP+/− mice. No significant difference in IGF-I levels was observed between GHR/BP+/+ and GHR/BP+/− mice.

e) GH Levels Are Dramatically Elevated in Homozygous GHR/BP−/− Mice

Figure 11:
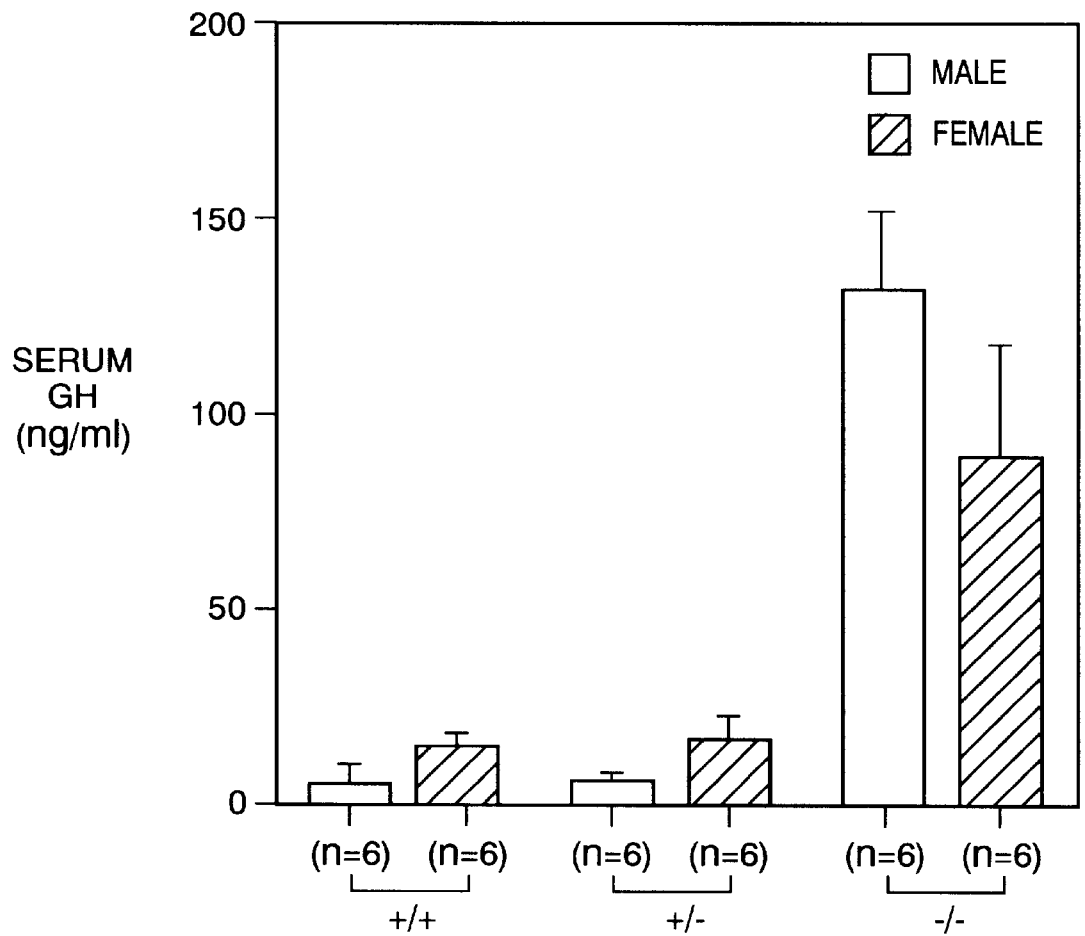
FIG. 11 is a graph showing serum GH levels in GHR/BP+/+, GHR/BP+/− and GHR/BP−/− mice.

Serum GH levels were determined by standard polyclonal radioimmunoassay [Sinha et al. (1972) Endocrinol. 91:784] using reagents supplied by the National H ormone and Pituitary Program; the assay s were performed according to the manufacturer's protocol. The results are summarized in FIG. 11. In FIG. 11, serum GH levels (ng/ml) are shown for male (shaded columns) and female (filled columns) normal (+/+), heterozygous (+/−) and homozygous (−/−) GHR/BP disrupte d mice.

As shown in FIG. 1, serum GH levels were dramatically increased in GHR/BP−/− mice as found in Laron syndrome patients, indicating negative feedback regulation of GH expression was impaired in these mice.

f) Blood Glucose Levels In GHR/BP Disrupted Mice

Blood glucose levels are measured using standard methods (e.g., One Touch II glucometer and One Touch glucose test strips, Lifescan, Milpitas, Calif.).

g) GHR And GHBP Expression In GHR/BP Knockout Mice

Expression of GHR and GHBP in tissues of heterozygous and homozygous GHR/BP knockout mice as well as wild-type control mice is determined by Northern blot analysis, RT-PCR analysis and radioreceptor binding assay.

i) Northern Blot Analysis

Tissues are dissected from mice immediately after decapitation. Total RNA is extracted using the standard guanidine thiocyanate procedure [Zhou et al. (1994) Receptor 4:143 and Wang et al. (1993) Mol. Cell. Endocrinol. 94:89]. Forty micrograms of each RNA sample is subjected to 1.5% formaldehyde agarose gel electrophoresis, and then transferred to nylon membrane (e.g., Genescreen plus, Dupont, Boston, Mass.). For GHR/BP mRNA determination, four hybridization probes representing the GHR extracellular domain (781 bases), the exon 8A GHBP region (140 bases), the 8A/8 region (1600 bases), and the intron 8/8A (287 bases) which have been previously described are employed [Zhou el al. (1994), supra and Zhou el al. (1994) Receptor 4:223]. These DNAs are radiolabeled with $\alpha^{32}$P-dNTPs using the random priming method. Hybridization is carried out in 50% formamide, 1% SDS, 1M NaCl and 10% dextran sulfate solution at 42° C. Following hybridization, the membrane is washed with 2x SSC/1% SDS and exposed to X-ray film.

For GHRH, SRIH, GH and GHRH-R mRNA determination in hypothalamus and pituitary, the following hybridization probes are used: full length GHRH, SRIH, and GH cDNAs and a 277 bp rGHRH-R cDNA which was generated by PCR and subsequently cloned. After high stringency washing, the signal is quantified by using a Fuji BAS1000 Phosphoimager.

ii) RT-PCR

To confirm that the GHR/BP gene was disrupted and did not express functional GHR and mGBP mRNA, RT-PCR was employed using RNA isolated from a variety of tissues such as liver, kidney, fat and muscle. Total RNA was isolated from mouse tissues as described in Northern blot analysis. Two hundred to 400 rig of total RNA was used for RT-PCR analysis using a RT-PCR kit (Perkin-Elmer, Norwalk, Conn.). The EX3+1 (5'-CCCCAGTTCTGCAAAGAATC-3'; SEQ ID NO: 16) and EX5-1 5'-GGGGTATCCAAATGGAGGTA-3'; SEQ ID NO:17) primer pair amplify a 299 bp fragment which corresponds to mRNA containing exons 3–5. The EX3+1 (SEQ ID NO:16) and EX6-1 (5'-CCTTCAGAACATCTGCATT-3'; SEQ ID NO:18) primer pair amplify a 488 bp fragment which corresponds to mRNA containing exons 3–6.

RT-PCR analysis confirmed the disruption of the mGHR/BP gene in homozygous GHR/BP–/– mice.

iii) Radioreceptor Binding Assay

Levels of GHR present in mouse tissues is determined as described [Chen et al. (1990) Proc. Natl. Acad. Sci. USA 87:5061]. Briefly, liver, kidney and muscle tissue isolated from knockout and control mice are homogenized with a Brinkean Polytron in 4 volumes (w/v) of ice-cold homogenization buffer (0.3 M sucrose, 10 mM EDTA, 50 mM HEPES, 0.1 mM TPCK and 1 mM PMSF at pH 8.0). All manipulations are carried out at 4° C. The homogenate is centrifuged at 20,000x g for 30 minutes and the supernatant is removed and then centrifuged at 100,000x g for 1 hour. The final pellets, containing microsomal membranes, are suspended in 10 mM HEPES, pH 8.0 at a protein concentration of 25 to 50 µg/µl. The microsomal membrane suspension is then used for receptor binding studies.

hGH is obtained from Eli Lilly (Indianapolis, Ind.) and radiolabelled with $^{125}$I-Na (Amersham) to specific activities of ~100 and ~40 µCi/µg using standard lactoperoxidase methodologies.

Competitive binding assays are performed as follows: microsomal membranes corresponding to 1 mg protein are incubated with ($^{125}$I-QGH (0.5 ng/ml) and with various amount of unlabeled hGH ranging from 1 ng to 1 µg in a total volume of 0.3 ml assay buffer (20 mM HEPES, 10 mM $CaCl_2$, 0.1% BSA, and 0.05% $NaN_3$, pH 8.0). After a 3 hour incubation at room temperature, the reaction is stopped by the addition of 1 ml of ice cold assay buffer followed by centrifugation at 10,000x g for 15 min. Membrane pellets are then counted for radioactivity. All assays are performed in triplicate and are repeated three times. The Student's t test is used to determine the statistical differences between GHR binding levels.

iv) Serum GHBP Analysis

Mouse serum (50–400 µl) was incubated with >98% monomeric $^{125}$I-hGH (~0.5 ng) in PBS (pH 7.4) in a final volume of 500 µl for 1 hr at 37° C. Bound GH was then separated from free GH by size exclusion chromatography [Baumann et al. (1986) J. Clinl. Endocrinol. Metab. 62:134] and the radioactive peak corresponding to the bound fraction was integrated. Non-specific binding was determined by parallel incubation in the presence of 2 µg/ml of unlabeled hGH. Specific binding was defined as the difference between total and non-specific binding. If necessary, final results were corrected for saturation by endogenous GH based on a saturation standard curve obtained with GH as described for hGH [Baumann et al. (1986), supra].

The above results demonstrate that homozygous GHR/BP–/– knockout mice provide an mammalian model of Laron syndrome. The homozygous GHR/BP–/– mice, like Laron syndrome patients, show growth retardation, have elevated serum levels of GH, low IGF-I levels and no detectable serum GHBP.

EXAMPLE 5

Production Of GHR Knockout Mice

Figure 12:
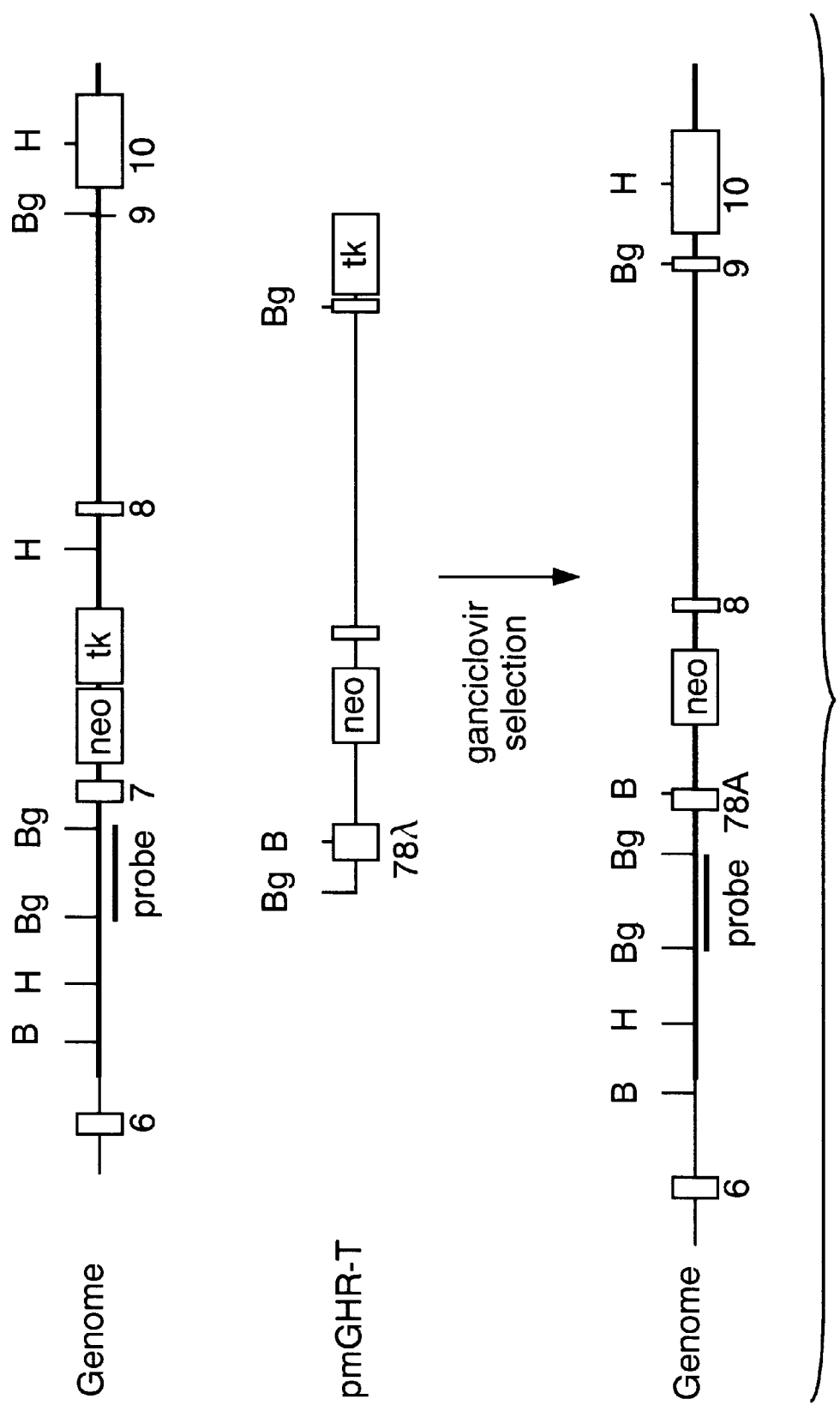
FIG. 12 provides a schematic showing the strategy for the specific disruption of the GHR gene (i.e., the generation of GHR knockouts).

Mice which lack the ability to express functional GHR, but which express functional GHBP, are produced as described below. A schematic showing the strategy for the specific disruption of the GHR gene (i.e., the generation of GHR knockouts) is provided in FIG. 12. The following abbreviations are used in FIG. 12: B, BamHI; Bg, BglII; and H, HindIII. The targeted deletion of the intron 7/8A permits the expression of GHBP but not GHR.

a) Construction Of A GHR Targeting Vector

The GHR targeting vector, pGHR-T, was generated from pGHBP-T. pGHBP-T was constructed as follows. The 8 kb BglII fragment of GHR/BP containing exon 8A and the flanking sequences was cloned into pUC18 (Gibco/BRL) which contains the M13 F1 origin of replication and is used to produce single stranded DNA for mutagenesis. The resulting plasmid was termed pGHBP-T.

To construct the pGHR-T targeting vector, the intron between exon 7 and 8A was removed from pGHBP-T by oligonucleotide directed mutagenesis, such that the end of exon 7 was directly joined to the beginning of exon 8A. The mutagenic primer has the following sequence: 5'-AGAATTGGACTTGGTTCCTTCTTCACATGC TTCC-3' (SEQ ID NO:19). In addition, a neo gene was inserted into the HindIII site located in intron 7/8 and a tk gene was inserted at the 3' end of the GHR/BP homologous sequence (FIG. 13).

b) Generation Of GHR Knockout ES Cells

ES cells containing a disrupted GHR allele are generated by electroporation of pGHR-T into ES cells which contain the homologously recombined pGHBP-T1 vector (i.e., the G418$^r$, GAN$^r$ ES cells generated from the first round of targeting in Ex. 5). Twenty-four hours after electroporation, ES cells are grown in medium containing G418 and gancyclovir to select for neo and against tk gene expression. The presence of the desired homologous recombination event in the G418r, GANG ES cells is confirmed by Southern blot analysis using HindIII digestion and the 1.0 kb BgIII probe (FIG. 13, "probe"). The presence of a homologous recombination event yields a band of approximately 15 kb as only the HindIII sites found in intron 6/7 and exon 10 will be present. If homologous recombination did not occur, HindIII digestion (located in intron 6/7 and intron 7/8) yields a band of 6 kb.

c) Generation And Characterization Of GHR Knockout Mice

The GHR disrupted ES cells are used to generate chimeric mice as described in Example 3. The chimeric mice are bred with normal Balb/c mice to produce heterozygous GHR knockout mice (Ex. 3). Heterozygous mice are interbred to produce homozygous GHR knockout mice. Heterozygosity and homozygosity are determined by Southern blot analysis.

The GHR knockout mice (homozygotes and heterozygotes) are characterized by examination of growth rate, IGF-I levels, and expression of GHR and GHBP as described in Example 4. Homozygous GHR−/− mice are expected to have elevated serum levels of GH, low IGF-I levels and show growth retardation. In contrast to the GHR/BP−/− mice, the GHR−/− mice will express serum GHBP (as do some human Laron syndrome patients). The GHR−/− mice provide an mammalian model of Laron syndrome.

EXAMPLE 6

Screening Of Chemical Compounds Using GHR/BP and GHR Knockout Mice

As discussed above mice which lack the ability to express the GHR or both the GHR and GHBP provide model systems for the screening of compounds having therapeutic benefit for the treatment of a variety of disease states including Laron syndrome, non-Laron syndrome forms of GH insensitivity (e.g., patients expressing GR which are insensitive to GH) and diabetes. As the GHR/BP−/− and GHR−/− mice lack the GHR, these mice can be used to identify compounds which modulate the second messenger or signalling pathways which act downstream of the binding of the ligand (GH) to its receptor (the GHR); these mice may also be used to identify compounds which modulate the second messenger or signalling pathways which act downstream of the binding of IGF-I to its receptor.

a) Identification Of Compounds Useful For the Treatment Of GH Insensitivity

Compounds are screened for the ability to effect growth rates (i.e., to increase or decrease growth) in the GHR/BP−/− and GHIR−/− mice as follows. Candidate compounds are administered to transgenic and non-transgenic littermates by injection (e.g., intravenous, intraperitoneal, intramuscular, sub-cutaneous), insertion of an implant capable of sustained delivery of the compound or orally (e.g., in the food or water supply). The compound(s) may be initially administered at various timepoints including at weaning and at 21 days of age and administration is continued until adulthood or about 1 year of age is reached. The body growth rate of the animals is determined as described in Ex. 4b. Compounds which increase the growth rate of the GHR/BP−/− and/or GHR−/− mice (i.e., transgenics) relative to control animals (i.e., transgenics and non-transgenics which did not receive the compound) are identified as compounds useful for the treatment of GH insensitivity, including Laron syndrome. In addition to measuring the body growth rate to determine whether the administered compounds are useful for the treatment of GH insensitivity, other clinical endpoints such as an increase in IGF-1 levels may be measured.

In addition to providing a means for screening compounds for the treatment of Laron syndrome as outlined above, the homozygous GHR/BP−/− mice provide an animal model to test gene replacement therapy protocols aimed at inserting a functional copy of the GHR and/or GHBP gene into various sites in an intact animal. These animals allow the optimization of gene replacement therapy for Laron syndrome (e.g., level of expression which must be achieved, number of sites which must be targeted, etc. to restore normal metabolism and growth).

b) Identification Of Compounds Useful For the Treatment Of Diabetes And Diabetic End Organ Damage As discussed above, elevated levels of GH are associated with the development of nephropathy in animals, including humans, which express the GHR. Therefore, signalling through the GHR is implicated in the development of kidney lesions in diabetics. One-third to one-half of the 20 million diabetic patients in the U.S. have kidney problems and diabetic nephropathy represents the leading cause for dialysis. The GHR/BP−/− and GHR−/− mice of the present invention provide model systems for the identification of compounds which disrupt the signalling pathways (downstream of the binding of GH to the GHR) which are involved in the development of diabetic nephropathy. Compounds which inhibit the progression of nephropathy are identified as follows.

GHR−/− and GHR/BP−/− mice (4 to 10 week old) are treated with streptozotocin (STZ; Sigma) to induce diabetes by injection of 50–100 μg STZ/g body wt-day; four to eight injections of STZ are given. Control animals are injected with 100 μl vehicle solution (citrate buffer)/g body wt-day. The mice are fed standard chow (e.g., Purina Rodent Chow 5004, Ralston Purina, St. Louis, Mo.). Blood glucose levels are determined each day during STZ treatment and each week after STZ treatment. Blood glucose is assayed as described in Ex. 4. Protein and glucose are measured in the urine of the STZ-treated and control mice using Ames Uristick (Miles Inc., Elkhart, Ind.). Animals displaying symptoms of diabetes [e.g., blood glucose levels of 300–500 mg/dl, glucosuria (urine glucose >1000 mg/dl)] are examined for evidence of kidney pathology (e.g., glymerulosclerosis) by examination of kidney histology as described [Chen et al. (1995) Endocrinol. 136:660]. Briefly, coronal kidney sections are fixed in Carnoy's fixatve, embedded in glycol methacrylate follwed by sectioning and staining with hematoxylin and eosin and acid-Schiff. Kidney pathology consistent with diabetic end organ damage includes large glomeruli, mesangial matrix expansion, glomerular cell proliferation, Kimmelstiel-Wilson (K-W) nodules and tubulointestinal lesions [Chen et al. (1995), supra].

A second set of animals is treated with STZ as described above with the exception that test compounds are administered (before, during and/or after STZ treatment) to determine the ability of these compounds to prevent kidney lesions associated with diabetes.

EXAMPLE 7

Identification of Alternative And/Or Tissue-Specific GHRs

It has been reported that the development of STZ-induced kidney lesions in mice is dependent upon the interaction of growth hormone with the growth hormone receptor [Chen et al. (1996) Endocrinol. 137:5163 and Chen et al. (1995), supra]. Therefore, if the GHR-/- and GHR/BP-/- mice develop kidney lesions in response to STZ treatment this indicates that a GHR different from the GHR that was disrupted in these knockout mice exists; such an alternative GHR may be a kidney-specific GHR. [for a discussion of alternative GHRs see, e.g., Mathews (1991) Trend. Endocrinol. Metab. 2:176] Thus, the GHR-/- and GHR/BP-/- mice provide a means for the identification of alternative GHRs and for the identification of compounds capable of interacting downstream of these alternative GHRs (i.e., capable of disrupting the signalling pathways downstream of the binding of GH to the alternative GHR).

It is clear from the above that the present invention provides mammalian models of Laron syndrome and GH insensitivity. In addition the transgenic animals of the present invention provide model systems for the screening of compounds having therapeutic benefit for the treatment of Laron syndrome as well as for the treatment and prevention of nephropathy.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

We claim:

1. A transgenic mouse whose genome comprises a disruption of the endogenous growth hormone receptor/binding protein gene, wherein said disruption comprises the insertion of a selectable marker sequence, and wherein said disruption results in said mouse exhibiting growth retardation as compared to a wild-type mouse.

2. The transgenic mouse of claim 1, wherein said disruption results in said mouse exhibiting undetectable levels of growth hormone receptor.

3. The transgenic mouse of claim 1, wherein said disruption results in said mouse producing reduced levels of growth hormone binding protein.

4. The transgenic mouse of claim 3, wherein said disruption results in said mouse exhibiting undetectable levels of growth hormone receptor.

5. The transgenic mouse of claim 1, wherein said disruption results in said mouse producing reduced levels of insulin-like growth factor-I.

6. The transgenic mouse of claim 1, wherein said selectable marker sequence is the neo gene.

7. A method for screening compounds for growth promoting activity, comprising:
   a) providing:
      i) a transgenic mouse whose genome comprises a disruption of the endogenous growth hormone receptor/binding protein gene, wherein said disruption comprises the insertion of a selectable marker sequence, and wherein said disruption results in said mouse exhibiting growth retardation as compared to a wild-type mouse; and
      ii) a composition comprising a test compound in a form suitable for administration to said transgenic mouse;
   b) administering said test compound to said transgenic mouse; and
   c) measuring an increase in the growth rate of said transgenic mouse as compared to untreated transgenic mice, and thereby identifying a compound as having growth promoting activity.

8. The method of claim 7, wherein said disruption results in said mouse exhibiting undetectable levels of growth hormone receptor.

9. The method of claim 7, wherein said disruption results in said mouse producing reduced levels of growth hormone binding protein.

10. The method of claim 9, wherein said disruption results in said mouse exhibiting undetectable levels of growth hormone binding protein.

11. A method for producing a transgenic mouse exhibiting growth retardation, comprising:
    a) providing
       i) a targeting vector comprising a selectable marker sequence, and
       ii) a mouse embryonic stem cell
    b) introducing said targeting vector into said mouse embryonic stem cell such that the endogenous growth hormone receptor/binding protein gene is disrupted by the insertion of the selectable marker sequence;
    c) injecting said mouse embryonic stem cell comprising the disruption into a blastocyst of a mouse; and
    d) introducing said injected blastocyst into a pseudopregnant mouse for the production of progeny, wherein the genome of the transgenic mouse of said progeny comprises said disruption of the endogenous growth hormone receptor/binding protein gene such that said transgenic mouse of said progeny exhibits growth retardation as compared to a wild-type mouse.

12. The method of claim 11, wherein said disruption in said progeny results in said progeny producing reduced levels of growth hormone binding protein.

13. The transgenic mouse of claim 1, wherein said disruption results in said mouse producing reduced levels of growth hormone receptor.

14. The method of claim 11, wherein said disruption in said progeny results in said progeny producing reduced levels of growth hormone receptor.

* * * * *